United States Patent
Reed et al.

(10) Patent No.: US 10,105,345 B2
(45) Date of Patent: *Oct. 23, 2018

(54) TANNIN-CONTAINING GASTROINTESTINAL FORMULATIONS AND METHODS OF USE

(71) Applicant: WISCONSIN ALUMNI RESEARCH FOUNDATION, Madison, WI (US)

(72) Inventors: Jess Dreher Reed, Madison, WI (US); Dhanansayan Shanmuganayagam, Madison, WI (US); Christian Gerald Krueger, Cambridge, WI (US); Kenneth Allan Kudsk, Madison, WI (US); Joseph Francis Pierre, Chicago, IL (US); Aaron F. Heneghan, Middleton, WI (US); Rodrigo P. Feliciano, Düsseldorf (DE)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,204

(22) Filed: Nov. 9, 2016

(65) Prior Publication Data

US 2017/0056369 A1 Mar. 2, 2017

Related U.S. Application Data

(63) Continuation of application No. 14/152,267, filed on Jan. 10, 2014, now Pat. No. 9,522,131.

(Continued)

(51) Int. Cl.
*A61K 31/353* (2006.01)
*A61K 9/00* (2006.01)
(Continued)

(52) U.S. Cl.
CPC ............ *A61K 31/353* (2013.01); *A23L 33/10* (2016.08); *A23L 33/115* (2016.08); *A23L 33/17* (2016.08);
(Continued)

(58) Field of Classification Search
CPC ........ A23L 33/10; A23L 33/17; A23L 33/115; A23L 33/40; A23V 2002/00; A61K 31/353; A61K 9/0029
See application file for complete search history.

(56) References Cited

U.S. PATENT DOCUMENTS

| 4,938,949 A | 7/1990 | Borch et al. |
| 5,229,136 A | 7/1993 | Mark et al. |

(Continued)

OTHER PUBLICATIONS

Li et al (Can. J. Physiol. Pharmacol. 86: 841-849 (2008)).*

(Continued)

*Primary Examiner* — Angela C Brown-Pettigrew
(74) *Attorney, Agent, or Firm* — Daniel A. Blasiole; DeWitt Ross & Stevens S.C.

(57) ABSTRACT

Tannin-containing compositions and methods of using same to enhance or maintain immune function during simplified nutrition feeding. Pharmaceutical compositions, including enteral nutrition compositions, are provided. The compositions comprise such tannins as proanthocyanidins and/or hydrolysable tannins. Administering the tannins to the gastrointestinal tract of a subject receiving simplified nutrition, such as with enteral nutrition therapy or parenteral nutrition therapy, attenuates or prevents deleterious effects on the gastrointestinal immune system that would otherwise occur with the simplified nutrition.

17 Claims, 10 Drawing Sheets

Related U.S. Application Data

(60) Provisional application No. 61/751,647, filed on Jan. 11, 2013.

(51) Int. Cl.
*A23L 33/00* (2016.01)
*A23L 33/10* (2016.01)
*A23L 33/17* (2016.01)
*A23L 33/115* (2016.01)

(52) U.S. Cl.
CPC ............ *A23L 33/40* (2016.08); *A61K 9/0029* (2013.01); *A23V 2002/00* (2013.01)

(56) References Cited

U.S. PATENT DOCUMENTS

| | | | |
|---|---|---|---|
| 5,723,446 | A | 3/1998 | Gray et al. |
| 6,420,572 | B1 | 7/2002 | Romanczyk, Jr. et al. |
| 7,122,574 | B2 | 10/2006 | Romanczyk, Jr. et al. |
| 7,196,065 | B2 | 3/2007 | Ernest |
| 7,758,893 | B2 | 7/2010 | Hageman et al. |
| 7,790,209 | B2 | 9/2010 | Ohmori et al. |

OTHER PUBLICATIONS

Joliett et al (Intensive Care Med (1998) 24:848-859).*
Beecher, Overview of Dietary Flavonoids: Nomenclature, Occurence and Intake, J. Nutrition (2003) 3248S-3254S.
Bergstrom et al., Muc2 Protects against Lethal Infectious Colitis by Disassociating Pathogenic and Commensal Bacteria from the Colonic Mucosa, PLoS Pathog (2010) 6:d1000902.
Braga et al, ESPEN Guidelines on parenteral nutrition: Surgery, Clinical Nutrition (2009) 28:378-386.
Conterno et al., Obesity and the gut microbiota: does up-regulating colonic fermentation protect against obesity and metabolic disease?, Genes Nutr. (2011) 6:241-260.
de Vrese et al., Probiotics, prebiotics, and synbiotics, Adv Biochem Eng Biotechnol (2008) 111:1-66.
Feng et al., Specific degree-of-polymerization of A-type proanthocyanidin oligomers impacts *Streptococcus mutans* glucan-mediated adhesion and transcriptome responses within biofilms, Biofouling (2013) 29(6):629-640.
Fisher et al., Automated approach for ribosomal intergenic spacer analysis of microbial diversity and its application to freshwater bacterial communities, App Environ Microbiol. (1999) 65(10):4630-4636.
Gauthier et al., Treatment of urinary tract infections among febrile young children with daily intravenous antibiotic therapy at a day treatment center, Pediatrics 2004; 114;e469, DOI: 10.1542/peds.2004-0421.
Guarner, Role of intestinal flora in health and disease Nutr Hosp. (2007) 22 Suppl 2:14-19.
Houde et al, Protective effects of grape seed proanthocyanidins against oxidative stress induced by lipopolysaccharides of periodontopathogens, J Periodontol (2006) 77(8):1371-1379.
Howell et al., Dosage effect on uropathogenic *Escherichia coli* anti-adhesion activity in urine following consumption of cranberry powder standardized for proanthocyanidin content: A multicentric randomized double blind study, BMC Infectious Disease (2010) 10:94.
Jepson et al., Cranberries for preventing urinary tract infections (Review) The Cochrane Collaboration Issue 4 (2009).
Kajiura et al., Change of intestinal microbiota with elemental diet and its impact on therapeutic effects in a murine model of chronic colitis, Dig. Dis. Sci (2009) 54(9):1892-1900.
Kang et al., p90 ribosomal S6 kinase 2 promotes invasion and metastasis of human head and neck squamous cell carcinoma cells, J. Clin. Invest. (2010) 120:1165-1177.
Kirby et al., Enteral and parenteral nutrition, (2011), http://patients.gi.org/topics/enteral-and-parenteral-nutrition/, accessed Sep. 29, 2015.
Kovacs et al., A systematic assessment of automated ribosomal intergenic spacer analysis (ARISA) as a tool for estimating bacterial richness, Res Microbiol (2010) 161(3):192-197.
Krueger et al., Matrix-assisted laser desorption/ionization time-of-flight mass spectrometry of heteropolyflavan-3-ols and glucosylated heteropolyflavans in sorghum [*Sorghum bicolor* (L.) Moench], J. Agric. Food Chem. (2003) 51:538-543.
Li et al., Effects of parenteral and enteral nutrition on gut-associated lymphoid tissue, J. Trauma (1995) 39:44-51.
MacCaferri et al., Metagenomics: key to human gut microbiota Dig. Dis. (2011) 29(6):525-530.
Martin et al., Development of a novel pomegranate standard and new method for the quantitative measurement of pomegranate polyphenols, J. Sci Food Agric (2009) 89:157-162.
McClave et al., Guidelines for the Provision and Assessment of Nutrition Support Therapy in the Adult Critically Ill Patient: Society of Critical Care Medicine (SCCM) and American Society for Parenteral and Enteral Nutrition (A.S.P.E.N.) Journal of Parenteral and Enteral Nutrition (2009) 33(3):277-316.
Monograph, Oligomeric proanthocyanidins (OPCs), Alternative Medicine Review (2003) 8(4):442-50.
Neto et al., MALDI-TOF MS Characterization of proanthocyanidins from cranberry fruit (*Vaccinium macrocarpon*) that inhibit tumor cell growth and matrix metalloproteinase expression in vitro, J. Sci. Food Agric. (2006) 86:18-25.
Ofman, et al., Clinical economics review: nutritional support, Ailment Pharmacol Ther (1997) 11:453-471.
Ott et al., Reduction in diversity of the colonic mucosa associated bacterial microflora in patients with active inflammatory bowel disease Gut (2004) 53(5):685-693.
Ottaviani et al., Intake of dietary procyanidins does not contribute to the pool of circulating flavanols in humans, Am J Clin Nutr (2012) 95(4):851-858.
Parrish et al., Enteral formula selection: A review of selected product categories, Practical Gastroenterology (2005) Series No. 28:44-74.
Parrish et al., Elemental and semi-elemental formulas: Are they superior to polymeric formulas? Practical Gastroenterology (2005) Series No. 34:59-72.
Pierre, Parenteral and elemental nutrition decreases intestine mucosal immunity, Which is partially restored by dietary proanthocyanidins and IL-25, (2012) Doctoral Thesis.
Pierre et al., Cranberry Proanthocyanidins Improve the Gut Mucous Layer Morphology and Function in Mice Receiving Elemental Enteral Nutrition) Journal of Parenteral and Enteral Nutrition (2013) 37(3):401-409, e-published Oct. 11, 2012.
Pierre et al., Cranberry Proanthocyanidins Improve Intestinal sIgA During Elemental Enteral Nutrition Journal of Parenteral and Enteral Nutrition (2013.
Porter et al., Cranberry proanthocyanidins associate with low-density lipoprotein and inhibit in vitro $Cu^{2+}$-induced oxidation, J. Sci Food Agric. (2001) 81:1306-13.
Preisner et al, Enteral feeding with a solution enriched with antioxidant vitamins A, C, and E enhances the resistance to oxidative stress, Crit Care Med (2000) 28(12): 3828-3832.
Quideau et al., Ellagitannin Chemistry, Chem. Rev. (1996) 96:475-503.
Reed et al., MALDI-TOF mass spectrometry of oligomeric food polyphenols, Phytochem (2005) 66:2248-2263.
Sano et al., Parenteral nutrition maintains pulmonary IgA antibody transport capacity, but not active transport, following injury, Am J. Surg. (2009) 198:105-109.
Scalbert et al., Dietary polyphenols and the prevention of diseases, Crit Rev Food Sci Nutr. (2005) 45(4):287-306.
Singleton et al., Colorimetry of Total Phenolics with Phosphomolybdic-Phosphotungstic Acid Reagents, Amer. J. Enology and Viticulture (1965) 16:144-58.
Sitren et al., Total parenteral nutrition in the mouse: development of a technique, J Parenter Enteral Nutr. (1983) 7:582-6.
Tuohy et al., Up-regulating the Human Intestinal Microbiome Using Whole Plant Foods, Polyphenos, and/or Fiber, J Agric Food Chem. (2012) 60(36):8776-8782.

(56) References Cited

OTHER PUBLICATIONS

Walpole et al., The weight of nations: An estimation of adult human biomass, BMC Public Health (2012) 12:439.
White et al., Proximate and polyphenolic characterization of cranberry pomace, J. Agric. Food Chem. (2010) 58:4030-6.
Yuste et al, The effect of proanthocyanidin-rich hulls and proanthocyanidin extracts from bean (*Vicia faba* L.) hulls on nutrient digestibility and digestive enzyme activities in young chicks, British Journal of Nutrition (1992), 67:57-65.

* cited by examiner

TANNIN-CONTAINING GASTROINTESTINAL FORMULATIONS AND METHODS OF USE

STATEMENT REGARDING FEDERALLY SPONSORED RESEARCH

This invention was made with government support under GM053439 awarded by the National Institutes of Health. The government has certain rights in the invention.

FIELD OF THE INVENTION

The present invention is directed to tannin-containing compositions for delivery to the gastrointestinal tract of a subject receiving simplified nutrition.

BACKGROUND

The gastrointestinal mucosa maintains a physical and chemical barrier against 100 trillion resident bacteria as well as food and environmental antigens. A number of interrelated factors influence this function, including mucus glycoproteins, antimicrobial molecules, specific and non-specific antibodies, enterocyte tight-junctions, and colonization of commensal microbiota. The dietary intake of the host affects the complex interplay between factors. The route and complexity of nutrition profoundly influences the mucosal immune system, specifically the mucosal associated lymphoid tissue.

Elemental enteral nutrition (EEN) or parenteral nutrition (PN) are useful therapeutic options for conditions requiring a reduced residual diet, including pancreatitis, inflammatory bowel disorders such as Crohn's disease, and a variety of other conditions (Ofman et al. Clinical economics review: nutritional support. *Ailment Pharmacol Ther* 1997, 11:453-471; and McClave et al. *Journal of Parenteral and Enteral Nutrition,* 33(3):277-316). A reduction in dietary intake or complexity, such as those that occur with elemental enteral or parenteral nutrition, decreases the number of lymphocytes in Peyer's patches and lamina propria, reduces levels of IgA-stimulating Th-2 type cytokines in the gut wall, and reduces levels of intestinal immunoglobulins (primarily IgA) compared to chow feeding or administration of a complex enteral diet containing complex carbohydrates, proteins, and fats. Elemental enteral and parenteral nutrition also increase barrier permeability and significantly suppress bacterial diversity within the gut. Elemental enteral or parenteral nutrition thus induce well-defined dysfunction of the mucosal immune system, specifically within the gut-associated lymphoid tissue (GALT), and suppress mucosal barrier function when compared to normal nutrition. The integrity of the mucosal barrier is critical for maintaining the physical and chemical barrier against microbes as well as food and environmental antigens. The mucosal barrier depends on multiple factors including the physical and compositional characteristics of the mucous layer, presence of antimicrobial compounds within the mucous layer, immunoglobulin (especially IgA) secretion by the mucosal immune cells, permeability of the enterocyte tight-junctions, and the commensal endogenous microbiota.

Tannins are a class of polyphenolic compounds widely distributed in plant-derived foods and beverages. Tannins are associated with beneficial health outcomes in epidemiological studies. Tannins are composed of two sub-classes, hydrolysable tannins and condensed (proanthocyanidin, PAC) tannins. Tannins have a propensity to bind proteins through hydrogen bonding. For example, proanthocyanidins form complexes with salivary glycoproteins, a process that causes astringency in the oral cavity when many fruits and beverages are ingested. This complexation increases salivary excretion, hypertrophy of the parotid gland, and a shift in salivary composition to proline-rich glycoproteins. Because of poor absorption, a large proportion (sometimes greater than 95%) of proanthocyanidins remains in the intestinal lumen during transit. Thus, beneficial dietary effects may occur through interactions at the mucosal surface of the gastrointestinal tract, for example, by influencing secretion of mucins, a class of glycoproteins, in the small intestine.

Mucins are secreted by goblet cells (GC) and play a critical role in maintaining mucosal integrity. Goblet cells are specialized intestinal epithelial cells. Goblet cells migrate up the villi after differentiating from crypt stem cells and turn over with the epithelial layer every 3-5 days. Mucin2 (MUC2) is the most abundant mucin secreted by intestinal goblet cells. The importance of MUC2 is underscored in MUC2−/− mice, in which the deficiency leads to the development of lethal colitis. MUC2 secretion is induced by cholinergic stimulation, while its production is regulated by IL-4 and IL-13 from T-helper 2 cells (Th-2) in the lamina propria or intraepithelial cells.

While the influence of dietary intake or complexity on mucosal barrier and immunity is appreciated, very little is known of the influence of "non-nutritive" dietary compounds, such as tannins. Accordingly, formulations and feeding methods that can counteract the deleterious effects of enteral or parenteral nutrition on modulators of mucosal barrier integrity are needed to provide more efficacious options for patents that require enteral nutrition, parenteral nutrition, and other restricted dietary regimens.

SUMMARY OF THE INVENTION

Compounds that counteract or prevent the deleterious effects of commonly used enteral or parenteral nutrition formulations have been discovered and are described herein. Specifically, the administration of various types of tannins, including proanthocyanidins and hydrolysable tannins, has been found to counteract the deleterious effects of enteral or parenteral nutrition on such outcomes as mucosal barrier integrity and mucosal immunity, among others.

Thus, the invention provides an enteral nutrition composition that includes a tannin. The composition may include, for example, calories from simple carbohydrates such as glucose, other monosaccharides, and/or disaccharides; amino acids; vitamins; minerals; fatty acids and/or fatty acid glyceryl esters; and a tannin. The composition may include, for example, a protein source comprising at least 20% of the total calories; a carbohydrate source comprising at least 30% of the total calories; and a lipid source comprising at least 30% of total calories; and an amount of tannins. Other possible formulations are described below. The amount of tannins in the composition can be an amount effective to attenuate the negative effects of enteral nutrition on intestinal barrier function or mucosal immunity when enteral nutrition is administered to a patient, where such enteral nutrition lacks the tannins described herein.

The enteral nutrition composition can be provided to a patient, for example, as a tube-fed enteral product. The composition can reduce the risk of diarrhea and other complications that arise from receiving nutrition only from an elemental enteral nutrition product. The enteral nutrition composition that includes tannins as described herein can meet the nutrient requirements of a variety of patients, such as sepsis patients, trauma, burn or post-surgery patients, and those on a prescribed restricted diet, including intensive care patients, who may have compromised absorption capacity, or any medical situation where enteral nutrition is prescribed, including preparation for surgery, or in patients with acute or chronic illness.

The invention also provides pharmaceutical compositions comprising tannins. The pharmaceutical compositions allow for the introduction of a bolus of a specially-formulated tannin mixture before/during/after feeding of simplified nutrition, such as in enteral or parenteral feeding. The tannin formulation can be administered orally in solid form. However, tube feeding of liquid forms may be advantageous to certain patient populations. The methods of administering the tannins can include concurrent administration (i.e., at the time of simplified nutrition feeding), prophylactic administration (i.e., introduction of tannins in advance of simplified nutrition feeding), or interventional administration (i.e., once problems develop).

Any of the compositions described herein can be substantially free of monomeric tannin components, such as single flavan-3-ol units, and/or hydrolysable tannins. The tannins may have degrees of polymerization of at least 2, at least 3, at least 4 or at least 5. The tannins in the compositions may be exclusively proanthocyanidins, exclusively hydrolysable tannins, or a combination of both. The proanthocyanidins may have at least one A-type interflavan bond, or at least one B-type interflavan bond.

Accordingly, one version of the invention comprises a composition for enteral nutrition. The composition comprises one or more nutrient components and a tannin. The one or more nutrient components comprise at least one of a nitrogen source and a carbohydrate source. A lipid source may optionally be included. The nitrogen source is selected from the group consisting of individual amino acids and polypeptides. At least about 10% by mass of the nitrogen source comprises a nitrogen source component selected from the group consisting of individual amino acids and polypeptides having an average chain length less than about 50 residues. The carbohydrate source comprises at least about 10% by mass of a carbohydrate source component selected from the group consisting of monosaccharides and disaccharides. The one or more nutrient components and the tannin may be comprised within a liquid carrier. The tannin may be present in an amount from about 0.1 mg/L to about 13 g/L.

Another version of the invention comprises a method of ameliorating a deleterious effect on immune function resulting from simplified nutrition. The method comprises administering an effective amount of a tannin to the gastrointestinal tract of a subject receiving a simplified nutrition composition. The simplified nutrition composition comprises one or more nutrient components comprising at least one of a nitrogen source and a carbohydrate source. A lipid source may optionally be included. The nitrogen source is selected from the group consisting of individual amino acids and polypeptides. At least about 10% by mass of the nitrogen source comprises a nitrogen source component selected from the group consisting of individual amino acids and polypeptides having an average chain length less than about 50 residues. The carbohydrate source comprises at least about 10% by mass of a carbohydrate source component selected from the group consisting of monosaccharides and disaccharides. The tannin may be administered in an amount of from about 1 mg/kg subject body weight per day to about 500 mg/kg subject body weight per day. The simplified nutrition composition may be administered as enteral or parenteral nutrition therapy. The tannin may be administered in a solid form or in a liquid form. If administered in a liquid form, the tannin may be present in an amount of from about 0.1 mg/L to about 13 g/L. The tannin may be administered as formulated in any enteral nutrition composition described herein. The tannin is preferably administered in an amount effective to increase ileal IL-4, ileal IL-13, goblet cell density, goblet cell size, luminal MUC2 concentration, Peyer's patch lymphocytes, STAT6 phosphorylation, polymeric immunoglobulin receptor (pIgR), luminal secretory immunoglobulin-A (sIgA), and/or gut microbiota diversity in the subject.

Another version of the invention comprises a method of ameliorating a deleterious effect on immune function resulting from enteral nutrition or parenteral nutrition. The method comprises administering an effective amount of a tannin to the gastrointestinal tract of a subject receiving enteral or parenteral nutrition therapy. The tannin may be administered in an amount of from about 1 mg/kg subject body weight per day to about 500 mg/kg subject body weight per day. The tannin may be administered in a solid form or in a liquid form. If administered in a liquid form, the tannin may be present in an amount of from about 0.1 mg/L to about 13 g/L. The tannin may be administered as formulated in any enteral nutrition composition described herein. The tannin is preferably administered in an amount effective to increase ileal IL-4, ileal IL-13, goblet cell density, goblet cell size, luminal MUC2 concentration, Peyer's patch lymphocytes, STAT6 phosphorylation, polymeric immunoglobulin receptor (pIgR), luminal secretory immunoglobulin-A (sIgA), and/or gut microbiota diversity in the subject.

Various additional non-limiting, exemplary versions of the invention include the following:

Version 1: A composition for enteral nutrition comprising: a tannin and one or more nutrient components comprising at least one of a nitrogen source and a carbohydrate source, wherein: (1) the nitrogen source is selected from the group consisting of individual amino acids and polypeptides, wherein at least about 10% by mass of the nitrogen source comprises a nitrogen source component selected from the group consisting of individual amino acids and polypeptides having an average chain length less than about 50 residues; and (2) the carbohydrate source comprises at least about 10% by mass of a carbohydrate source component selected from the group consisting of monosaccharides and disaccharides.

Version 2: The composition of version 1 wherein the one or more nutrient components comprises the nitrogen source and wherein at least about 10% by mass of the nitrogen source comprises individual amino acids.

Version 3: The composition of version 1 wherein the one or more nutrient components comprises the carbohydrate source and the carbohydrate source comprises at least about 30% by mass of the carbohydrate source component selected from the group consisting of monosaccharides and disaccharides.

Version 4: The composition of version 1 wherein the one or more nutrient components and the tannin are comprised within a liquid carrier.

Version 5: The composition of version 4 wherein the tannin is present in an amount from about 0.1 mg/L to about 13 g/L.

Version 6: The composition of version 1 wherein the tannin comprises a proanthocyanidin.

Version 7: The composition of version 1 wherein the tannin comprises a hydrolysable tannin.

Version 8: The composition of version 1 wherein the composition is substantially free of monomeric tannin components.

Version 9: A method of ameliorating a deleterious effect on immune function resulting from simplified nutrition comprising administering an effective amount of a tannin to the gastrointestinal tract of a subject receiving a simplified nutrition composition, wherein the simplified nutrition composition comprises one or more nutrient components comprising at least one of a nitrogen source and a carbohydrate source, wherein: (1) the nitrogen source is selected from the group consisting of individual amino acids and polypeptides, wherein at least about 10% by mass of the nitrogen source comprises a nitrogen source component selected from the group consisting of individual amino acids and polypeptides having an average chain length less than about 50 residues; and (2) the carbohydrate source comprises at least about 10% by mass of a carbohydrate source component selected from the group consisting of monosaccharides and disaccharides.

Version 10: The method of version 9 wherein the simplified nutrition composition is administered to the subject via a tube directly to the gastrointestinal tract.

Version 11: The method of version 9 wherein the simplified nutrition composition is administered to the subject parenterally.

Version 12: The method of version 9 wherein the tannin comprises a proanthocyanidin.

Version 13: The composition of version 9 wherein the tannin comprises a hydrolysable tannin.

Version 14: The composition of version 9 wherein the composition is substantially free of monomeric tannin components.

Version 15: The method of version 9 comprising administering the tannin in an amount of from about 1 mg/kg subject body weight per day to about 500 mg/kg subject body weight per day.

Version 16: The method of version 9 wherein the tannin is administered in a solid form.

Version 17: The method of version 9 wherein the tannin is administered in a liquid form.

Version 18: The method of version 17 wherein the tannin is present in an amount of from about 0.1 mg/L to about 13 g/L.

Version 19: The method of version 9 wherein the simplified nutrition composition, when administered in the absence of the tannin, decreases at least one of ileal IL-4, ileal IL-13, goblet cell density, goblet cell size, luminal MUC2 concentration, Peyer's patch lymphocytes, STAT6 phosphorylation, polymeric immunoglobulin receptor (pIgR), luminal secretory immunoglobulin-A (sIgA), and gut microbiota diversity in the subject.

Version 20: The method of version 9 wherein the effective amount of the tannin is an amount effective to increase at least one of ileal IL-4, ileal IL-13, goblet cell density, goblet cell size, luminal MUC2 concentration, Peyer's patch lymphocytes, STAT6 phosphorylation, polymeric immunoglobulin receptor (pIgR), luminal secretory immunoglobulin-A (sIgA), and gut microbiota diversity in the subject.

The objects and advantages of the invention will appear more fully from the following detailed description of the preferred embodiment of the invention made in conjunction with the accompanying drawings.

For FIGS. 1-5, the data is presented as mean±SEM, and the superscript "a" denotes significance of difference when compared to chow feeding, while the superscript "b" denotes significance of difference when compared to EEN feeding alone.

Figure 6:
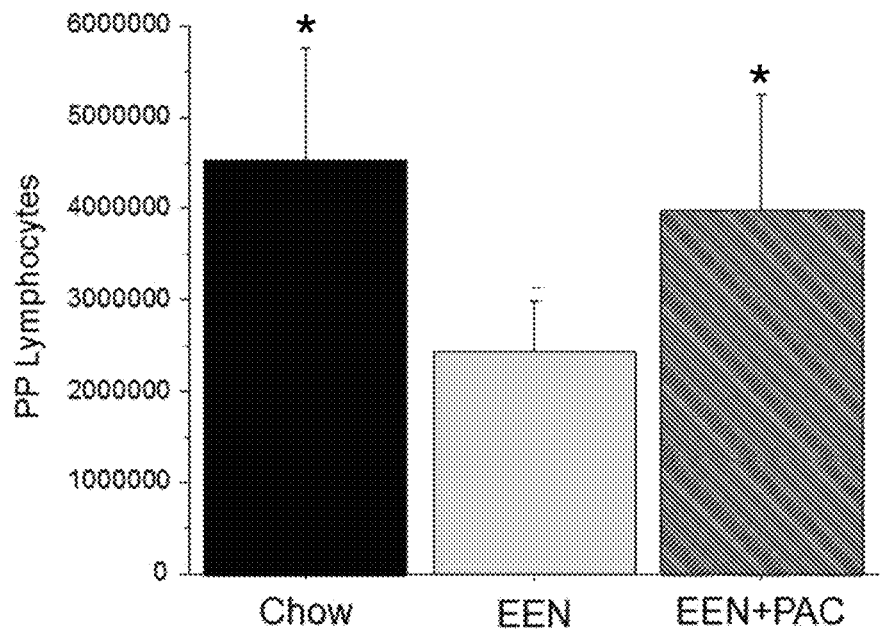

FIG. 6 depicts the total number of Peyer's Patch lymphocytes in chow, EEN, and EEN+proanthocyanidin (PAC) fed mice. *P<0.001 vs. EEN.

Figure 7:
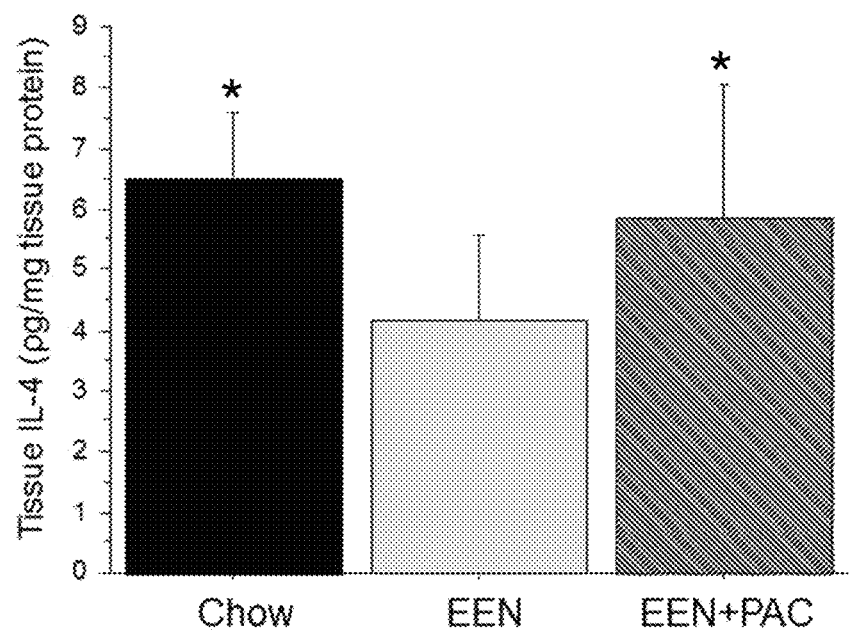

FIG. 7 depicts ileum tissue IL-4 levels in chow, EEN, and EEN+PAC fed mice. *P<0.05 vs. EEN.

Figure 8A:
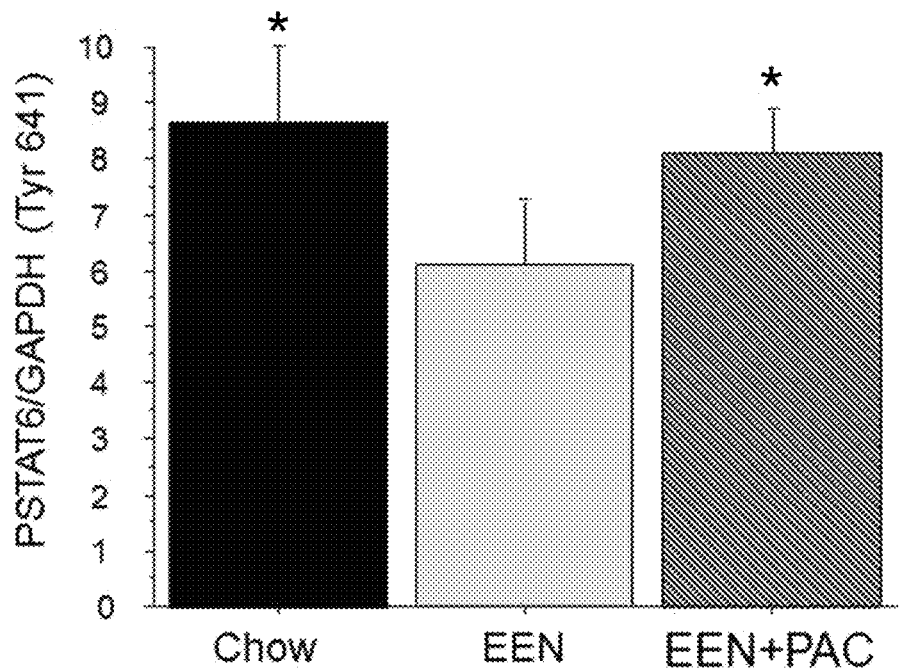
Figure 8B:
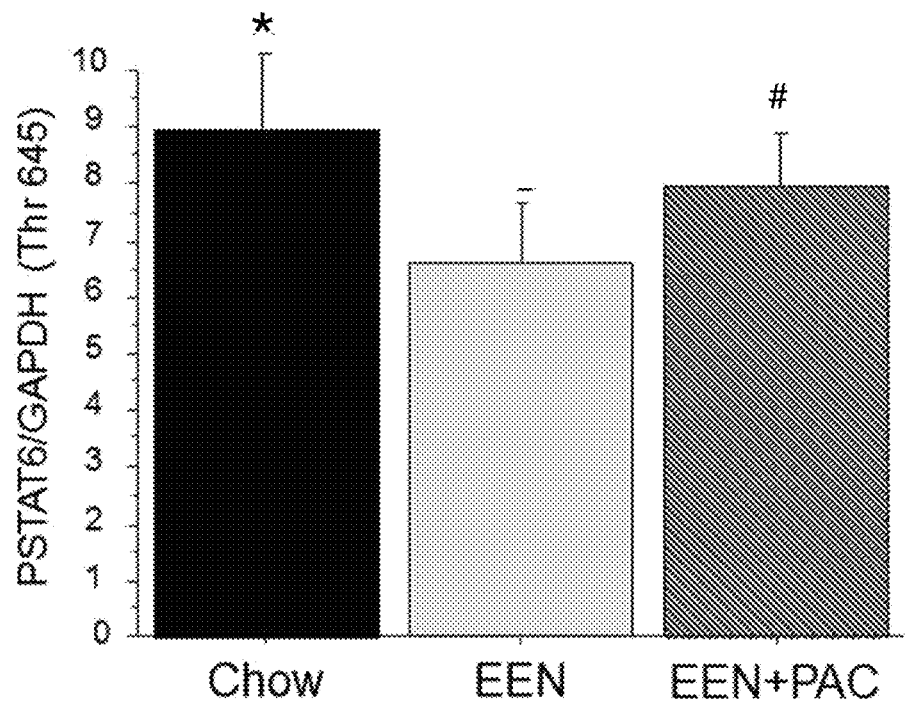

FIG. 8A depicts ileum tissue phosphorylated STAT6 (Tyr 641) levels in chow, EEN, and EEN+PAC fed mice. FIG. 8B depicts ileum tissue phosphorylated STAT6 (Tyr 645) levels in chow, EEN, and EEN+PAC fed mice. *P<0.01 vs. EEN. # P<0.05 vs. EEN.

Figure 9:
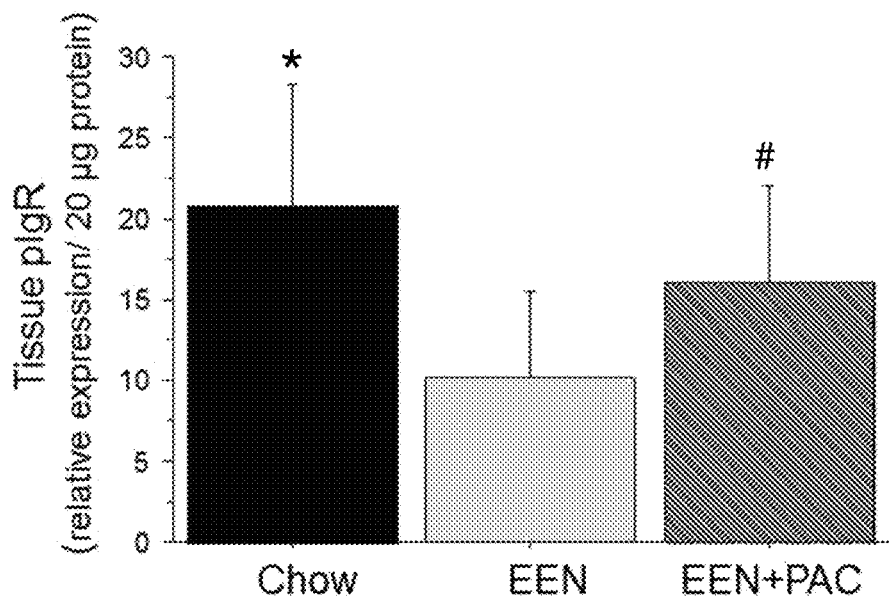

FIG. 9 depicts ileum tissue levels of polymeric immunoglobulin receptor (pIgR) in Chow, EEN, and EEN+PAC fed mice. *P<0.05 vs. EEN. # P<0.05 vs. EEN.

Figure 10:
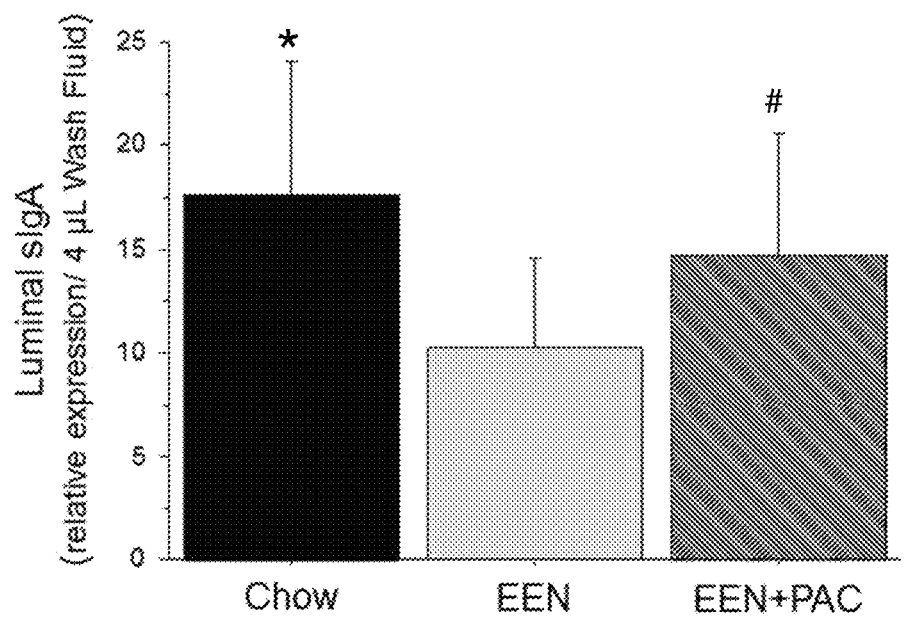

FIG. 10 depicts concentration of secretory IgA in small intestine luminal wash samples in Chow, EEN, and EEN+PAC fed mice. *P<0.01 vs. EEN. # P<0.05 vs. EEN.

Figure 11A:
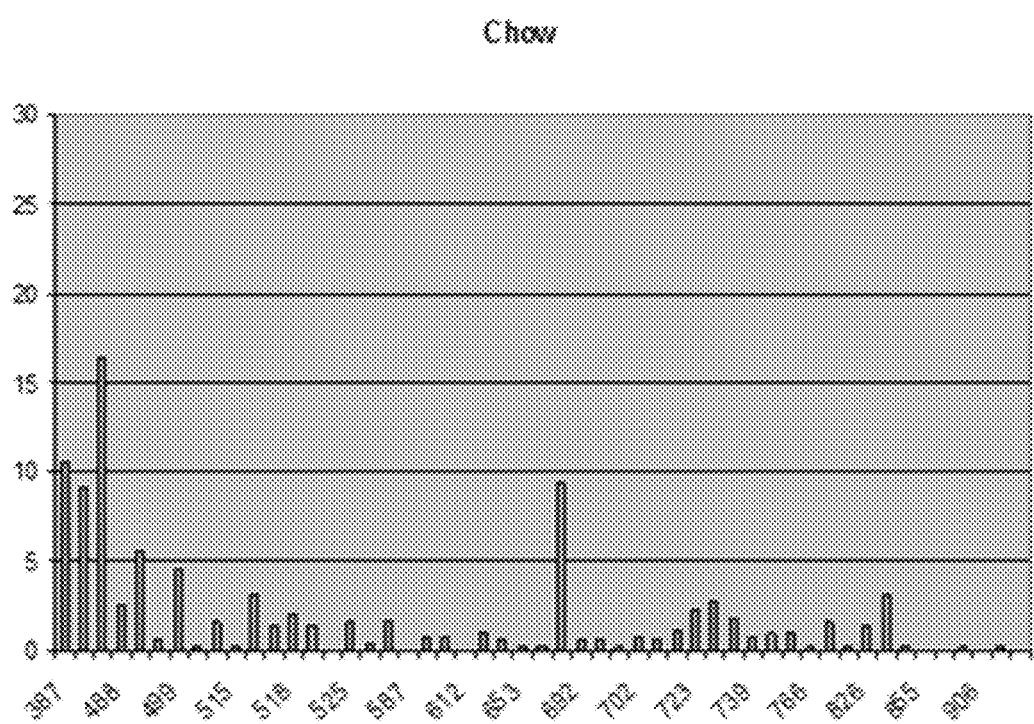
Figure 11B:
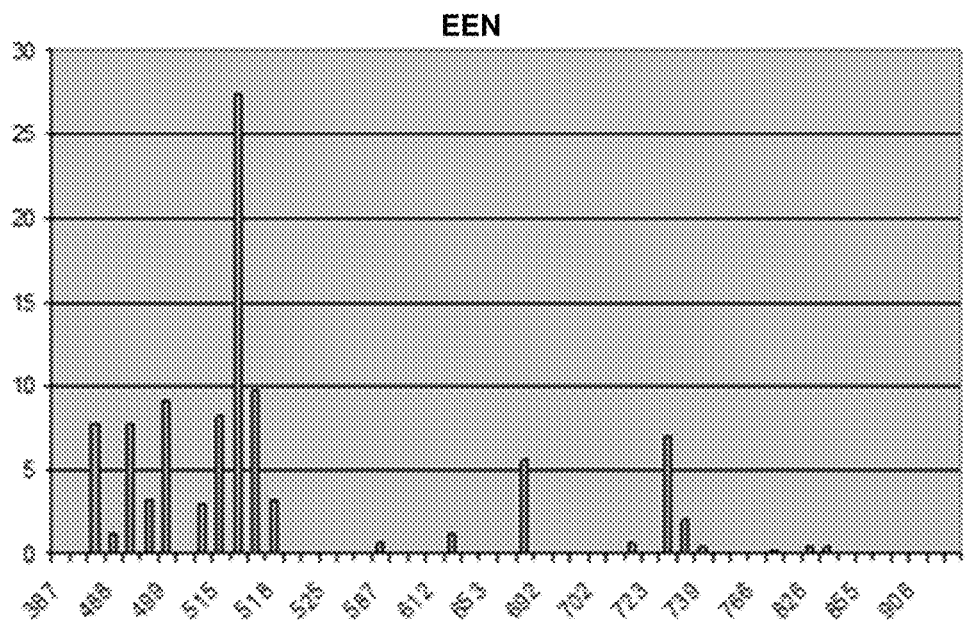
Figure 11C:
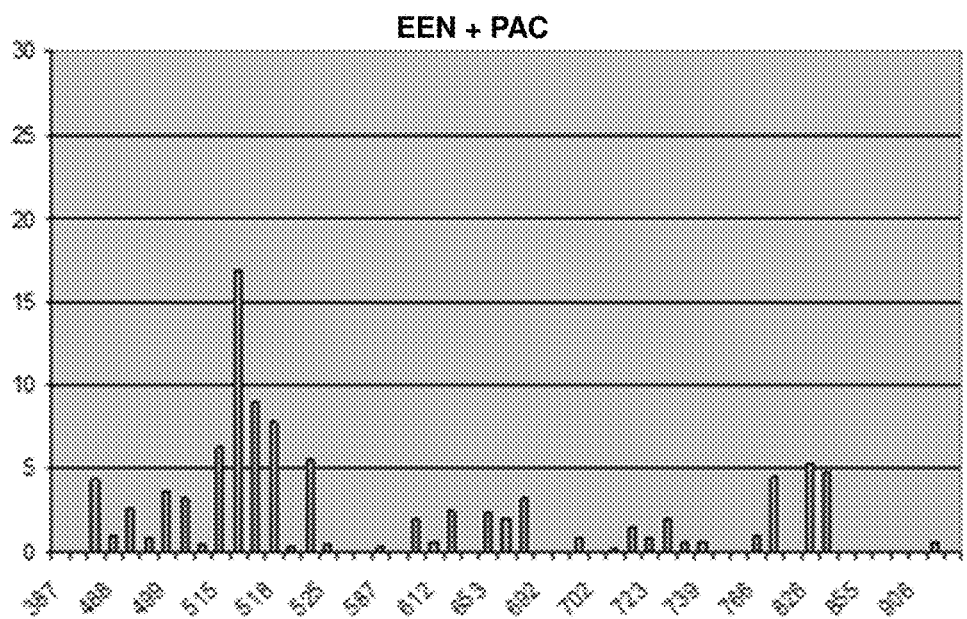

FIGS. 11A-C depict peaks observed greater than 0.5% of total signal as determined from automated ribosomal intergenic spacer analysis (ARISA) in intestinal content from the ileal-cecal junction of chow (FIG. 11A), EEN (FIG. 11B), and EEN+PAC (FIG. 11C) fed mice.

Figure 12:
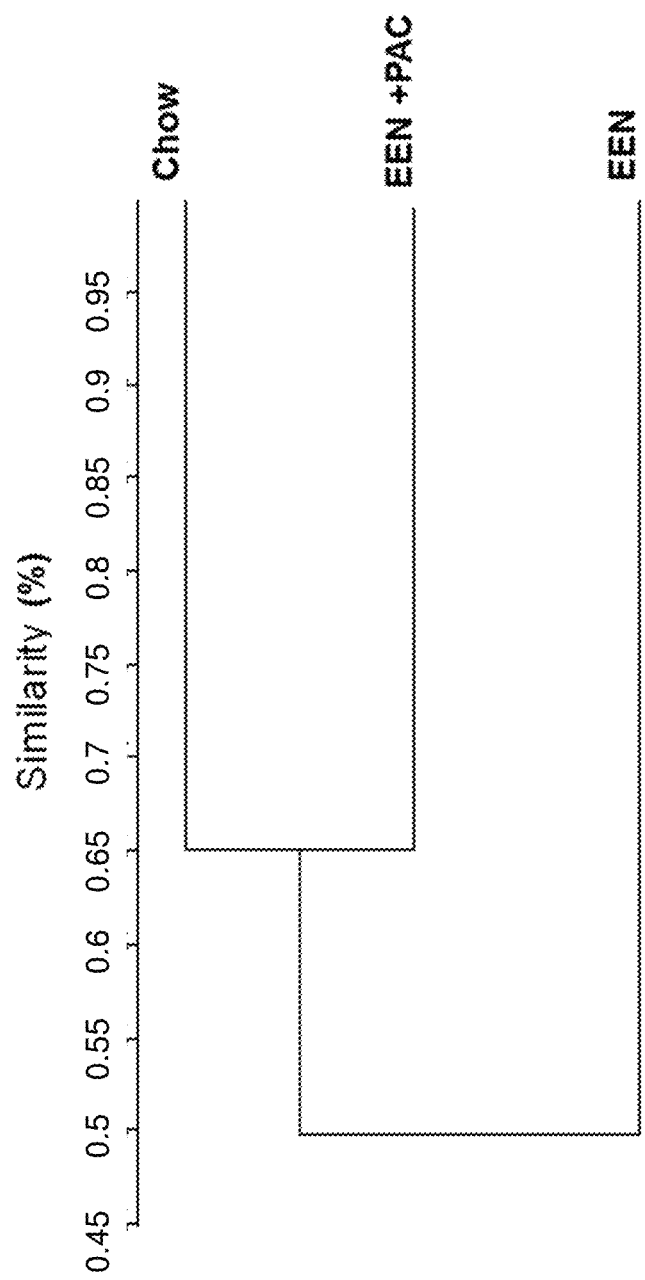

FIG. 12 depicts a dendrogram illustrating microbiome Jaccard's similarity coefficients between chow, EEN, and EEN+PAC fed mice. The results illustrate the greatest similarity between chow and EEN+PAC.

Figure 13:
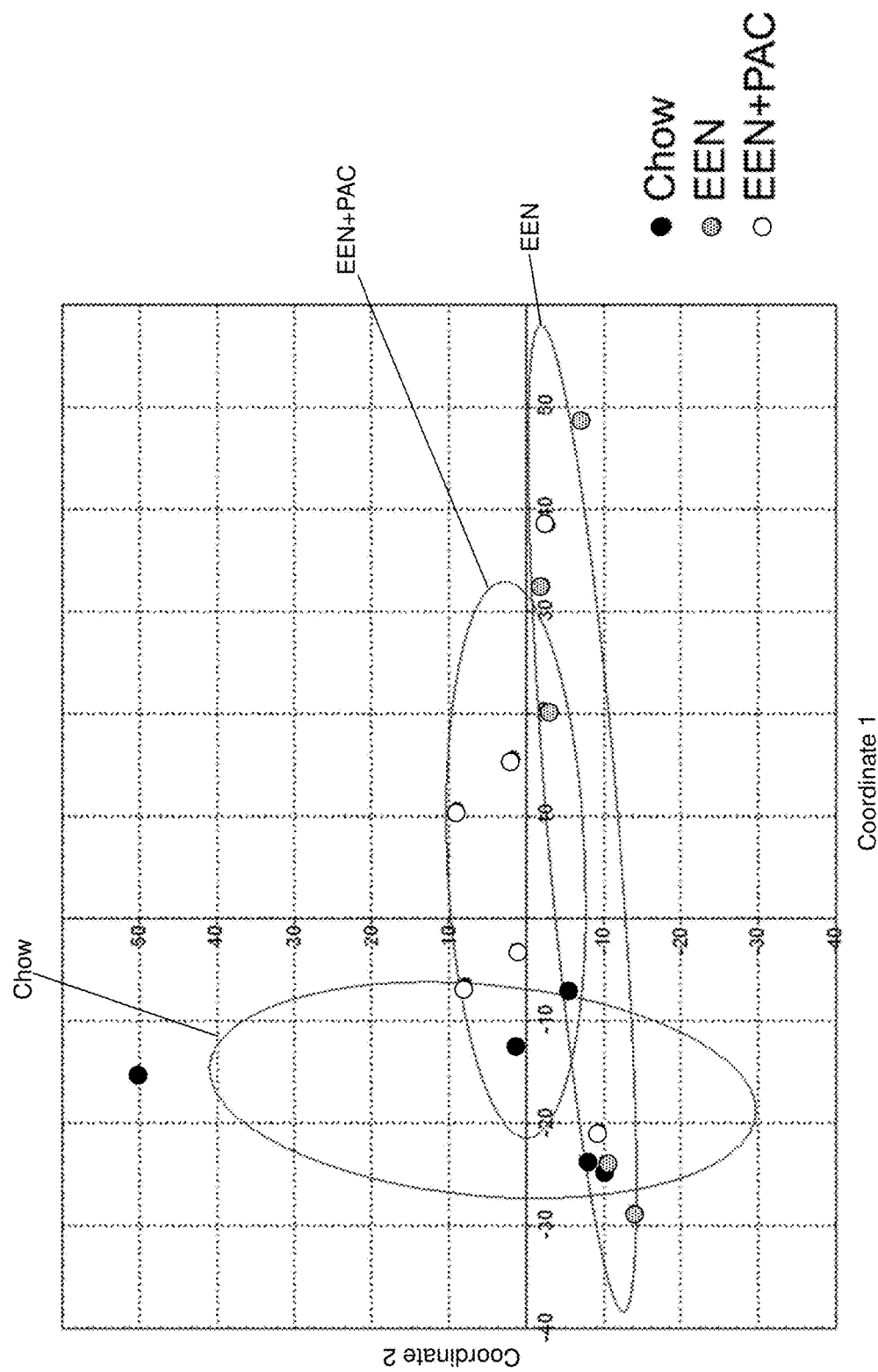

FIG. 13 depicts the results of principal coordinate analysis of chow, EEN, and EEN+PAC fed mice. Ellipses are 95% confidence.

DETAILED DESCRIPTION OF THE INVENTION

The gastrointestinal mucosa maintains a physical and chemical barrier against 100 trillion resident bacteria as well as food and environmental antigens. The dietary intake of a host affects the complex interplay among the many factors that influence the function of this barrier. A reduction in dietary intake or complexity, such as that which occurs with parenteral nutrition (i.e., IV feeding) or enteral nutrition (i.e., tube feeding), reduces the cellular and molecular functionality of the mucosal immune system in the intestines. Accordingly, enteral or parenteral nutrition significantly suppresses the mucosal immune system and increases the risk of infections and related complications, by increasing mucosal barrier permeability, and suppressing bacterial diversity within the gut.

Tannins are complex oligomeric polyphenolic compounds widely distributed in fruits, including grapes, cranberries, and apples, and other foods and beverages such as chocolate and wine. As described in the examples that follow, tannin preparations were isolated from various sources and added to an elemental enteral nutrition formulation. Adding the tannin to the elemental enteral nutrition formulation was found to counteract the deleterious effect of elemental enteral nutrition on modulators of mucosal barrier integrity.

The chemical nature of the tannins used in the compositions described herein allow the tannins to associate with the mucous layer of the gastrointestinal tract, delaying their clearance and thus providing a long-lasting beneficial effect on the immune system between enteral or parenteral feedings. Furthermore, due to the complexity and diversity of tannin chemistry, defined tannin preparations with defined biological effects can be prepared for use in enteral nutrition formulations. As the gastrointestinal tract poorly absorbs these plant-derived tannins, they are not believed to have problems associated with systemic toxicity.

Some current enteral compositions, such as the enteral product described by U.S. Pat. No. 5,229,136 (Mark et al.), provide an enteral product for reducing diarrhea in tube-fed patients. The product includes specific nutrient blends, including a high fiber content (greater than 14 g/mL), wherein the fiber can include components such as pectin, carob pods, and tannin-enriched extracts of carob pod. The high fiber content of the product (because of the amount of fiber/mL) would provide a highly viscous composition that may be problematic for the general tube-fed patient population. The tannin compositions described herein can alleviate these problems.

Definitions

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more tannins can refer to one or two, one to three, one to five, or one to about ten, different tannins, for example, having different degrees of polymerization.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "patient" or "subject" refers to any animal, such as a mammal, including mice, rats, other rodents, rabbits, dogs, cats, swine, cattle, sheep, horses, and/or primates, for example, humans.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a subject. Thus, an "effective amount" generally means an amount that provides the desired effect.

The terms "treating", "treat" and "treatment" include (i) preventing a disease, pathologic condition or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, or condition. The inhibition can be greater than about 20%, 40%, 60%, 80%, 90%, 95%, or 99%, for example, compared to the growth or progression that occurs in the absence of the treatment or contacting.

In reference to tannins, the phrase "substantially free of monomeric components" means that the tannins are at least dimeric in composition and few or no monomeric tannin species are present in the sample. For example, a tannin that is substantially free of monomeric components can include less than about 5 wt. % monomeric tannins, less than about 3 wt. % monomeric tannins, less than about 1 wt. % monomeric tannins, less than about 0.5 wt. % monomeric tannins, less than about 0.1 wt. % monomeric tannins, or no monomeric tannins. An example of a monomeric tannin is the compound tannic acid (pentagalloyl-D-glucose ($C_{76}H_{52}O_{46}$, mw=1701.18)). Other compounds that can be specifically included or excluded from the composites described herein include catechin (mw=290.26), quercetin (mw=302.24), cyanidin (mw=287.24), gelatin, epichlorohydrin moieties, or combinations thereof.

Improving mucosal immune function and mucosal barrier function in a patient refers to reducing factors that produce a changes associated with the suppression of mucosal immune function, including lower levels of Th2 stimulating cytokines, IL 4 and IL 13, lower goblet cell density and size, lower luminal MUC2 levels in the ileum, lower numbers of Peyer's patch lymphocytes, lower levels of STAT6 phosphorylation, lower levels of polymeric immunoglobulin receptor (pIgR), lower levels of luminal secretory immunoglobulin-A (sIgA), and/or reduced gut microbiota diversity. Thus, improving mucosal immune function and mucosal barrier function in a patient can refer to increasing levels of the Th2 stimulating cytokines, IL-4 and IL-13, increasing goblet cell density and size, increasing luminal MUC2 levels in the ileum, increasing numbers of Peyer's patch lymphocytes, increasing levels of STAT6 phosphorylation, increasing levels of polymeric immunoglobulin receptor (pIgR), increasing levels of luminal secretory immunoglobulin-A (sIgA), and/or increasing gut microbiota diversity.

Mucosal system functional indicators can include fecal or gastrointestinal luminal levels and/or composition of mucins, secretory immunoglobulin A (sIgA) or microbiome.

Enteral nutrition refers to nutritional support given via the alimentary canal or any route connected to the gastrointestinal system (i.e., the enteral route), for example, where nutrients are administered in a liquid carrier directly into the gastrointestinal (GI) tract, most commonly through a tube (i.e., tube feeding). Enteral nutrition (EN) is often used to prevent progressive malnutrition in patients with contraindication to normal feeding. Elemental enteral nutrition (EEN) is a nutritional support strategy utilized to treat patients with gastrointestinal disorders and inflammatory bowel disease, for example, typically with a drastically simplified diet that eliminates the complexity offered by whole foods and beverages. Elemental enteral nutrition suppresses the mucosal immune system by decreasing Peyer's patch density, lamina propria lymphocytes, Th2 cytokines, and IgA while increasing mucosal barrier permeability. The mucosal barrier is regulated in-part by mucins secreted by specialized epithelial cells called goblet cells (GC). The primary goblet cell mucin is mucin2 (MUC2) and deficiency of MUC2 leads to lethal colitis. MUC2 production is stimulated by the Th2 cytokines IL-4 and IL-13.

Parenteral nutrition (PN) refers to compositions and the administration thereof where nutrients are provided parenterally (e.g., intravenously) such that the nutrients bypass the gastrointestinal tract completely. Unfortunately parenteral nutrition feeding is associated with an increased risk of infection compared to enteral diets, especially in the critically ill, thus improvements in the current formulations are needed.

Tannins

Tannins include oligomeric polyphenols that occur naturally in a variety of plants. Isolated tannins typically form a heterogeneous mixture of tannin compounds. Tannin compounds can be subdivided into two groups: condensed tannins, also known as proanthocyanidins (PAC), and hydrolysable tannins (HT). The tannins used in the compositions described herein may comprise any one or more proanthocyanidin, any one or more hydrolysable tannin, or any combination of one or more proanthocyanidin and one or more hydrolysable tannin.

Proanthocyanidins are complex oligomeric polyphenolics widely distributed in plant sources such as cranberries and other sources. Tannin oligomers typically occur as dimers, trimers, tetramers, pentamers, hexamers, heptamers, octamers, nonamers, or decamers. Oligomers with greater than ten monomeric segments can also be isolated or synthesized, such as oligomers that include up to 50 units, as described herein. For a review of tannin nomenclature, see Beecher (J. Nutrition 2003, 3248S-3254S), which is incorporated herein by reference. In some embodiments, certain monomeric tannins or tannins with a low degree of polymerization can be excluded from a particular composition. For example, a composition may exclude catechin, tannic acid, or other monomeric tannins, dimeric tannins, trimers, or tetramers, PA tannins, or alternatively, hydrolysable tannins, a certain molecular weight range of tannins, or a type, class, or specific tannin cited in Beecher.

Proanthocyanidins are polymers of flavan-3-ols and flavans linked through interflavan bonds. Proanthocyanidins can have various types of interflavan linkages, including B-type and A-type linkages. B-type interflavan linkages are defined by the presence of C4→C8 or C4→C6 interflavan bonds. A-type interflavan linkages are defined by the presence of C4→C8 and C2→O→C7 interflavan bonds. The linkages can be α or β.

Monomers that may polymerized in the proanthocyanidins include, without limitation, catechin, epicatechin, epigallocatechin, epicatechin gallate, epigallocatechin gallate, epiafzelechin, fisetinidol, guibourtinidol, mesquitol, and robinetinidol, among others. Various flavonols may also be included as monomers in the proanthocyanidins, particularly as terminal units.

Various proanthocyanidin subtypes include, without limitation, prodelphinidins, proguibourtinidins, prorobinetinidins, proteracacinidins, and profisetinidins, among others.

The proanthocyanidins may be glycosylated with any glycone moiety at one or more positions, such as on an otherwise pendant hydroxyl group. Types of glycone moieties include, without limitation, glycopyranosyl glycones, furanosyl glycones, oligosaccharides (diglycosides, triglycosides, etc.), and amino glycone derivatives. Examples of glycopyranosyl structures include glucuronic acid, glucose, mannose, galactose, gulose, allose, altrose, idose, and talose. Examples of furanosyl structures include those derived from fructose, arabinose, or xylose. Examples of diglycosides (i.e., glycone moieties with 2 glycone units) include sucrose, cellobiose, maltose, lactose, trehalose, gentiobiose, and melibiose. Examples of triglycosides (i.e., glycone moieties with 3 glycone units) include raffinose or gentianose. Examples of amino derivatives include N-acetyl-D-galactosamine, N-acetyl-D-glucosamine, N-acetyl-D-mannosamine, N-acetylneuraminic acid, D-glucosamine, lyxosylamine, D-galactosamine, and the like.

Other chemical modifications of the pendant hydroxyl groups are acceptable.

The proanthocyanidins can have any degree of polymerization, such as 1 to about 50, 1 to about 25, 1 to about 20, 1 to about 12, 1 to about 10, 2 to about 50, 2 to about 25, 2 to about 20, 2 to about 12, 2 to about 10, or any range between any integers from 1 to about 50, including any range between any integers from 2 to about 50.

At least a subset of the proanthocyanidins suitable for use in the present invention may comprise one or more units of:

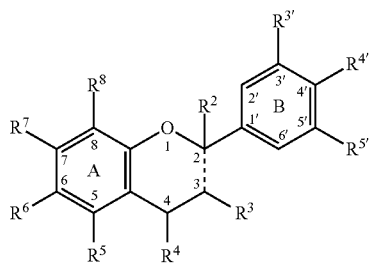

wherein:

------ is a single or double bond;

$R^5$ and $R^{3'}$-$R^{5'}$ are each independently —H, —OH, —O-glycoside, alkyloxy, alkanoyl, or alkanoyloxy;

$R^4$ is —H, =O, a C4-C6 inter-unit bond, or a C4-C8 inter-unit bond;

$R^6$ is —H or C6-C4 inter-unit bond;

$R^7$ is —H, —OH, —O-glycoside, alkyloxy, alkanoyl, or alkanoyloxy, or a C7-O—C2 inter-unit bond;

$R^8$ is —H, —OH, —O-glycoside, alkyloxy, alkanoyl, or alkanoyloxy, or a C8-C4 inter-unit bond $R^2$ is H or a C2-O—C7 inter-unit bond;

$R^3$ is —H, —OH, —O-glycoside, alkyloxy, alkanoyl, alkanoyloxy, or:

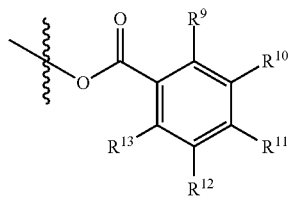

wherein $R^9$-$R^{13}$ are each independently —H, —OH, —O-glycoside, or alkyloxy, alkanoyl, or alkanoyloxy, provided that $R^9$-$R^{13}$ are not simultaneously hydrogen.

Scheme 1 illustrates an exemplary cranberry polyflavan-3-ol showing structural variation in the nature of interflavan linkage and substitution to an anthocyanin terminal unit through a $CH_3$—CH bridge.

Scheme 1. Representative structure of a proanthocyanidin (PAC).

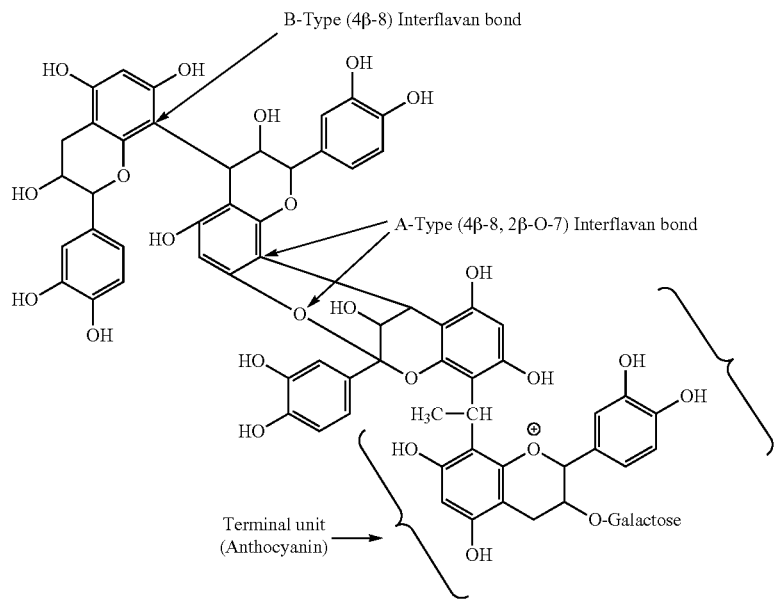

Scheme 1 shows a representative structure of a proanthocyanidin dimer linked to an anthocyanin through an ethyl (methine methyl) group. Variation in degree of polymerization, position and number of A-type versus B-type interflavan bonds and substitutions with anthocyanins leads to large structural heterogeneity among PAC oligomers.

Scheme 2 illustrates two sub-types of proanthocyanidin: procyanidins and prodelphinidins (for the trimer x=1; for the tetramer, x=2; for the pentamer, x=3; for the hexamer, x=4; for the heptamer, x=5; for the octamer, x=6; for the nonamer, x=7; and for the decamer, x=8). Procyanidins (R=H) contain catechin and/or epicatechin (CE) subunits; prodelphinidins (R=OH) contain gallocatechin and/or epigallocatchin (GE) subunits.

Scheme 2. Representative structure of a proanthocyanidin.
R = H and/or OH.

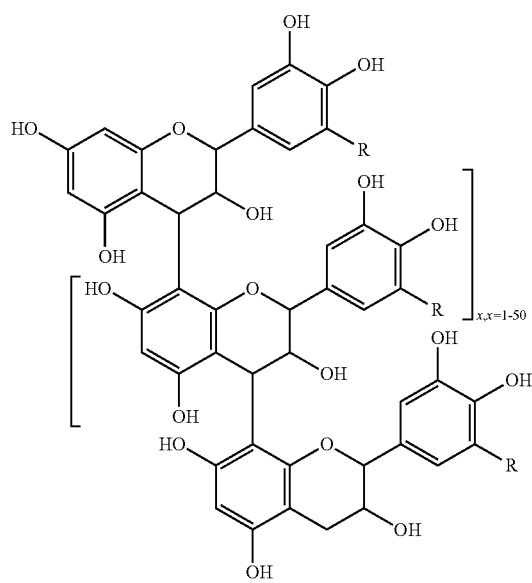

In various proanthocyanidins, the R groups of Scheme 2 can each independently be H or OH. In some embodiments, one or more hydroxyl groups may be glycosylated. In some embodiments, x is 1 to about 50, 1 to about 25, 1 to about 20, 1 to about 12, 1 to about 10, or a range of between any integers from 1 to 50.

Other proanthocyanidin tannins include glycosylated heteropolyflavans, such as those illustrated in Scheme 3. Representative compounds shown in Scheme 3 include proluteolinidin (R1=OH); proapigininidin (R1=H); eriodictyol (R2=H); and eriodictyol 5-O-β glucoside (R2=glucose). Krueger et al. have described a variety of known heteropolyflavans-3-ols and glycosylated heteropolyflavans (see J. Agric. Food Chem. 2003, 51, 538-543, which is incorporated herein by reference).

Scheme 3. Representative structure of a proanthocyanidins.

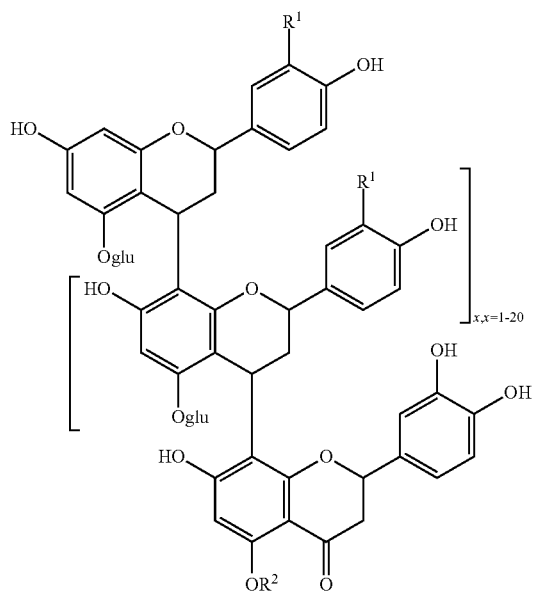

where R1 is H or OH; R2 is H or glucose; and glu is glucose (e.g., a β-glucoside).

In some embodiments, x of Scheme 3 is 1 to about 50, 1 to about 25, 1 to about 20, 1 to about 12, 1 to about 10, or a range of between any to integers from 1 to 50. Several examples of condensed tannins are described in U.S. Pat. No. 7,122,574 (Romanczyk et al.), which is incorporated herein by reference. A review by Reed et al. (Phytochem. 66(18): 2248-2263 (2005)) describes the structural heterogeneity of tannin polyphenols from cranberries, grape seed extracts, sorghum, and pomegranates as characterized by MALDI-TOF MS. Examples of plants that produce proanthocyanidins include cranberries, blueberries, grapes, sorghum, and pine.

Scheme 4 shows an additional example of a proanthocyanidin, which is an oligomer of three flavan-3-ol subunits.

Scheme 4. Proanthocyanidin trimer with three flavan-3-ol units linked by 4 → 8 carbon bonds.

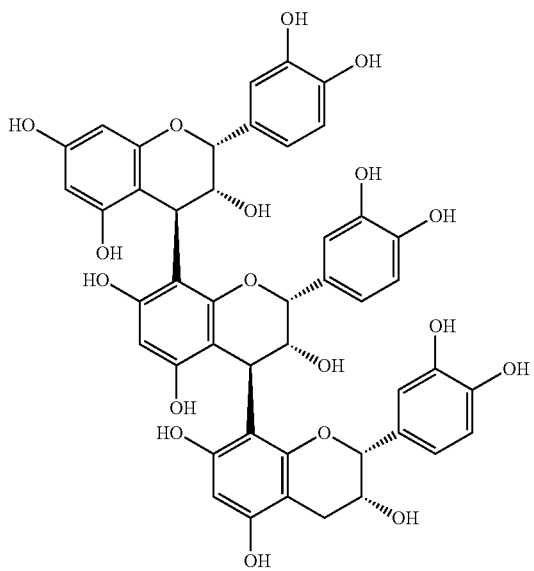

A review by Reed et al. (*Phytochem.* 66(18): 2248-2263 (2005)) describes the structural heterogeneity of tannin polyphenols from cranberries, grape seed extracts, sorghum, and pomegranates as characterized by MALDI-TOF MS. Examples of plants that produce proanthocyanidins include cranberries, blueberries, grapes, sorghum, and pine.

The proanthocyanidins suitable for use in the invention may comprise any proanthocyanidin described herein, known in the art, found in nature, or synthesized in a laboratory. A method for synthesizing proanthocyanidins is described in U.S. Pat. No. 6,420,572 to Romanczyk Jr. et al.

Hydrolysable tannins include esters of polyol core moieties, such as sugars. The sugar is usually D-glucose but may include other sugars such as cyclitols, quinic acid, shikimic acids, glucitol, hammamelose, and quercitol, among others. The hydroxyl groups of the sugar are partially or totally esterified with phenolic groups such as gallic acid, polymeric galloyl esters thereof, and/or oxidatively cross-linked galloyl groups, such as ellagic acid and gallagic acid. Gallotannins, for example, are polygalloyl esters, and ellagitannins are ellagic acid esters. Hydrolyzable tannins can be hydrolyzed by weak acids or weak bases to produce carbohydrate and phenolic acids.

Scheme 5 illustrates a pomegranate ellagitannin showing structural variation in nature of esterification of the glucose core molecule.

Scheme 5. Representative structure of a hydrolysable tannin.

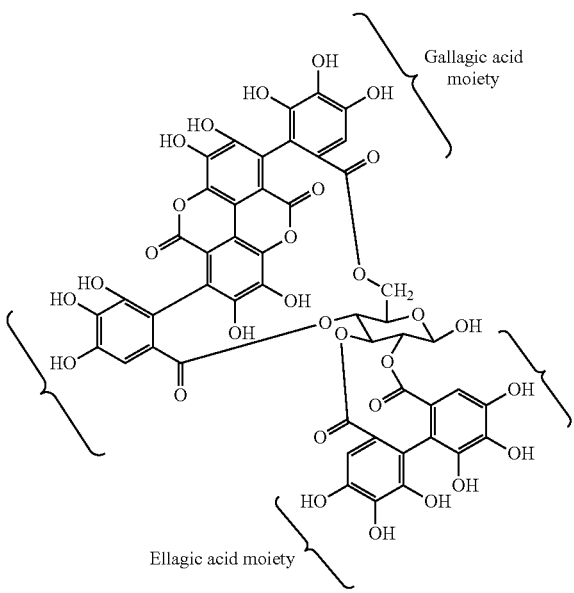

Hydrolysable tannins, such as the compound shown in Scheme 5, can be isolated in oligomeric forms that include 2 to about 12 hydrolysable tannin moieties, for example, linked by oxidative C—O coupling between galloyl and hexahydroxydiphenoyl moieties of the monomeric precursors. Common coupling also occurs between two ellagic acid moieties, or by addition of gallic acid moieties to the saccharide core of an oligomer. See Quideau and Feldman, *Chem. Rev.* 1996, 96, 475-503, which is incorporated herein in its entirety.

Accordingly, in some embodiments of compositions described herein, the hydrolysable tannins employed will be oligomeric hydrolysable tannins. Thus, in some embodiments, oligomeric hydrolysable tannins include at least two saccharide core moieties. Other embodiments can include monomeric hydrolysable tannins, and yet other embodiments can exclude monomeric tannins. In some embodiments, a hydrolysable tannin will include one or more (e.g., 1, 2, 3, 4, 5, or more) ellagic acid moieties, and in some embodiments, a hydrolysable tannin will include one or more (e.g., 1, 2, 3, 4, 5, or more) gallagic acid moieties.

Examples of plants that produce hydrolysable tannins include pomegranates, strawberries, raspberries, blackberries, sumac (*Rhus coriaria*), chestnut wood (*Castanea sativa*), oak wood (*Quercus robur*, *Quercus petraea* and *Quercus alba*), tara pods (*Caesalpinia spinosa*), gallnuts (*Quercus infectoria* and *Rhus semialata*), myrobalan (*Terminalia chebula*), and Aleppo gallnuts (*Andricus kollari*), among others. Significant quantities of hydrolysable tannins can be isolated from, for example, pomegranate husks. Specific hydrolysable tannins from pomegranates include punicalin and punicalagin (the alpha or beta isomer of 2,3-(S)-hexahydroxydiphenoyl-4,6-(S,S)-gallagyl-D-glucose, with a molecular weight of 1084) and stereochemical isomers thereof (see Martin et al. *J. Sci. Food. Agric.* 2009, 89:157-162). Other hydrolysable tannins are described by Quideau and Feldman (*Chem. Rev.* 1996, 96, 475-503).

As with the proanthocyanidins, the pendent hydroxyl groups on the condensed tannins may be glycosylated or otherwise modified.

The tannins suitable for use in the invention may comprise any proanthocyanidin or hydrolysable tannin described herein, known in the art, found in nature, or synthesized or modified in a laboratory. Methods for synthesizing proanthocyanidins and hyrolysable tannins are known in the art. See, e.g., U.S. Pat. No. 6,420,572 to Romanczyk Jr. et al.

Enteral Tannin Compositions and Administration Thereof

The tannins described herein can be added in effective amounts to enteral formulations and administered to a patient during enteral nutrition therapy using standard techniques, such as through the nasogastric system.

The enteral compositions may comprise one or more of a nitrogen source, a carbohydrate source, and a lipid source.

The nitrogen source is preferably in the form of individual amino acids and/or polypeptides. Exemplary nitrogen sources include casein, caseinates, soy protein, whey protein, lactalbumin, milk protein concentrate, hydrolyzed casein, hydrolyzed soy protein, hydrolyzed whey protein, hydrolyzed lactablumin, hydrolyzed milk protein concentrate and/or crystalline L-amino acids.

In elemental enteral formulations, the nitrogen source is exclusively comprised of individual amino acids or primarily comprised of individual amino acids and polypeptides having a short chain length. In various versions of the invention, for example, at least about 1% by mass, at least about 5% by mass, at least about 10% by mass, at least about 20% by mass, at least about 30% by mass, at least about 40% by mass, at least about 50% by mass, at least about 60% by mass, at least about 70% by mass, at least about 80% by mass, at least about 90% by mass, at least about 95% by mass, or at least about 99% by mass of the nitrogen source is comprised of either individual amino acids or individual amino acids in combination with polypeptides having, on average, a short chain length. As used herein, "short chain length" may refer to a chain length less than about 50 residues, less than about 40 residues, less than about 30 residues, less than about 20 residues, less than about 10 residues, less than about 5 residues, or less than about 3 residues. Methods of determining the proportion and size of amino acids and/or polypeptides in a composition are known in the art.

If present in the composition, the nitrogen source may comprise up to about 99% of the caloric content of the composition, such as about 1-99% of the caloric content of the composition, about 10-70% of the caloric content of the composition, or about 15-60% of the caloric content of the composition. Some compositions of the invention may be substantially devoid of a nitrogen source, such as amino acids or polypeptides.

The carbohydrate source may comprise any combination of simple carbohydrates (i.e., monosaccharides and disaccharides) and complex carbohydrates. Exemplary carbohydrate sources include glucose, sucrose, fructose, dextrose, glucose polymers, starches such as corn starch or hydrolyzed cornstarch, dextrin, maltodextrin, and sugar alcohols.

Compositions for elemental enteral nutrition preferably have a high proportion of simple carbohydrates. In various versions of the invention, for example, at least about 1% by mass, at least about 5% by mass, at least about 10% by mass, at least about 20% by mass, at least about 30% by mass, at least about 40% by mass, at least about 50% by mass, at least about 60% by mass, at least about 70% by mass, at least about 80% by mass, at least about 90% by mass, at least about 95% by mass, or at least about 99% by mass of the carbohydrate source is comprised of monosaccharides or a combination of monosaccharides and disaccharides.

If present in the composition, the carbohydrate source may comprise up to about 99% of the caloric content of the composition, such as about 1-99% of the caloric content of the composition, about 10-80% of the caloric content of the composition, or about 20-70% of the caloric content of the composition. Some compositions of the invention may be substantially devoid of a carbohydrate source.

The lipid source preferably comprises free fatty acids and/or glycerides (i.e., monoglycerides, diglycerides, and triglycerides). Exemplary lipid sources include fatty acid esters, fish oil, medium chain triglycerides, safflower oil, sardine oil, soybean oil, soy lecithin, structured lipids, borage oil, canola oil, corn oil, fish oil, high oleic sunflower oil, medium chain triglycerides, menhaden oil, mono- and diglycerides, palm kernel oil, safflower oil, soybean oil, soy lecithin, omega-3 fatty acids, and omega-6 fatty acids.

Compositions for elemental enteral nutrition are preferably low in fat with a small proportion of calories being derived from long-chain fatty acid lipids. In various versions of the invention, for example, the lipid source comprises less than about 1% by mass, less than about 5% by mass, less than about 10% by mass, less than about 20% by mass, less than about 30% by mass, less than about 40% by mass, less than about 50% by mass less than about 60% by mass, less than about 70% by mass, less than about 80% by mass, less than about 90% by mass, less than about 95% by mass, or less than about 99% by mass of long-chain fatty acid lipids. In some versions, the lipid source is substantially devoid of long-chain fatty acid lipids.

Compositions for elemental enteral nutrition typically replace long-chain fatty acid lipids with short- or medium-chain fatty acid lipids. Accordingly, in various versions of the invention, at least about 1% by mass, at least about 5% by mass, at least about 10% by mass, at least about 20% by mass, at least about 30% by mass, at least about 40% by mass, at least about 50% by mass, at least about 60% by mass, at least about 70% by mass, at least about 80% by mass, at least about 90% by mass, at least about 95% by mass, or at least about 99% by mass of the lipid source is comprised of short- or medium-chain fatty acid lipids.

As used herein, "short-chain fatty acid lipid" refers to a fatty acid moiety-containing lipid (i.e., free fatty acid, cholesterol ester, phospholipid, glyceride, etc.) with all fatty acid moieties containing fewer than 6 aliphatic carbons; "medium-chain fatty acid lipid" refers to a fatty acid moiety-containing lipid with all fatty acid moieties containing fewer than 12 aliphatic carbons; and "long-chain fatty acid lipid" refers to a fatty acid moiety-containing lipid with at least one fatty acid moiety comprising more than 12 aliphatic carbons.

If present in the composition, the lipid source may comprise up to about 99% of the caloric content of the composition, such as about 1-99% of the caloric content of the composition, about 10-70% of the caloric content of the composition, or about 20-60% of the caloric content of the composition. Some compositions of the invention may be substantially devoid of a lipid source.

The various proportions of the nitrogen source, the carbohydrate source, and the lipid source may be adjusted based on the nutritional or medical needs of the subject. For example, some compositions may comprise about 40% of caloric content as a carbohydrate source, about 20% of caloric content as a nitrogen source, and about 40% of caloric content as a lipid source. Others may comprise about 60% of caloric content as a carbohydrate source, about 30% of caloric content as a nitrogen source, and about 20% of caloric content as a lipid source. Others may comprise about 80% of caloric content as a carbohydrate source, about 10% of caloric content as a nitrogen source, and about 10% of caloric content as a lipid source. Certain enteral compositions can contain about 17-25% of the total calories from a nitrogen source, about 35-50% of total calories from a nitrogen source, and about 25-48% of total calories from a carbohydrate source.

The caloric density of the enteral nutrition composition is preferably at least about 1 Kcal/mL, at least about 1.2 Kcal/mL, at least about 1.3 Kcal/mL, at least about 1.5 Kcal/mL, or about 1.3-1.5 Kcal/mL.

The enteral nutrition composition may comprise proanthocyanidins, hydrolysable tannins, or a mixture of both.

The enteral nutrition composition of the invention can be provided in liquid form or dehydrated (powder) form, the latter of which may be mixed with a liquid carrier, such as water, before administering.

The enteral nutrition composition may comprise any effective amount of the tannin. Exemplary amounts of tannin in a liquid form of the composition include at least about 0.01 mg/L, at least about 0.1 mg/L, at least about 0.5 mg/L, at least about 1 mg/L, at least about 5 mg/L, or at least about 10 mg/L. Exemplary amounts of tannin in a liquid form of the composition may additionally or alternatively include less than about 15 g/L, less than about 13 g/L, less than about 10 g/L, less than about 1 g/L, or less than about 100 mg/L. If the composition is provided in dehydrated form, the composition preferably comprises an amount of tannin to comprise the above-listed concentrations when mixed with an appropriate amount solvent or liquid carrier for the desired caloric needs of the subject. Exemplary amounts of tannin in a dehydrated form include at least about 0.01% w/v, at least about 0.1% w/v, at least about 0.5% w/v, at least about 1% w/v, at least about 5% w/v, or at least about 10% w/v. Exemplary amounts of tannin in a dehydrated form of the composition may additionally or alternatively include less than about 100 g/L, less than about 50% w/v, less than about 25% w/v, less than about 15% w/v, less than about 13% w/v, less than about 10% w/v, less than about 1% w/v, or less than about 0.1% w/v.

In addition to the tannins, the enteral nutrition composition can include fiber, such as insoluble soy polysaccharide, insoluble pectin, hydrolyzed plant gums, carob pod, and/or extracts of carob pods. The composition can also optionally include one or more of the vitamins and minerals recommended by the US RDA. Exemplary vitamins and minerals are provided in the following examples. The composition can also include additional additives that can aid the health or immune function of a subject and benefit the subject's digestive tract. Such additives can include, for example, cellulose fiber, IL-25, rutin, D(+)-catechin, ellagic acid, quercetin, or curcumin, for elevating immunoglobulin A.

Examples of products that can be combined with the tannins described herein include the enteral formulations described by U.S. Pat. No. 5,229,136 to Mark et al.; U.S. Pat. No. 5,723,446 to Gray et al.; U.S. Pat. No. 7,196,065 to Ernest; U.S. Pat. No. 7,790,209 to Ohmori et al.; U.S. Pat. No. 7,758,893 to Hageman et al.; Makola, Elemental and Semi-Elemental Formulas: Are They Superior to Polymeric Formulas? *Practical Gastroenterology*, December 2005, in Nutrition Issues in Gastroenterology, Series #34, Ed. Parrish; and Malone, Enteral Formula Selection: A Review of Selected Product Categories. *Practical Gastroenterology*, June 2005, in Nutrition Issues in Gastroenterology, Series #28, Ed. Parrish.

The enteral nutrition composition may be administered via a tube into the gastrointestinal tract that extends at least through the mouth or that extends at least through the mouth and throat.

Pharmaceutical Compositions and Administration Thereof

The tannins described herein can be formulated as pharmaceutical compositions and administered to a mammalian subject, such as a human patient, in a variety of forms. The forms can be adapted for administration either orally or rectally to the gastrointestinal tract. The tannins can be administered in either a solid or a liquid form.

The pharmaceutical compositions may be prepared by any of the methods well known in the art of pharmacy. All methods include the step of bringing the tannins into association with a pharmaceutically acceptable carrier. A carrier is pharmaceutically acceptable if compatible with other ingredients in the particular composition and not deleterious to the recipient thereof. In general, the compositions are prepared by uniformly and intimately bringing the tannins into association with a liquid or solid carrier and then, if necessary, shaping the product into a desired unit dosage form.

Pharmaceutical compositions of the present invention suitable for oral administration may be presented in a discrete solid form, e.g., as capsules, hard or soft shell gelatin capsules, troches, cachets, tablets, boluses, wafers, lozenges and the like, each containing a predetermined amount of the tannin; in powder or granular form; or in liquid form, e.g., as a collyrium, suspension, solution, syrup, elixir, emulsion, dispersion and the like. A tablet may be made by compression or molding, optionally with one or more accessory ingredients. Compressed tablets may be prepared by compressing in a suitable machine the tannins in a free-flowing form, e.g., a powder or granules, optionally mixed with accessory ingredients or excipients, e.g., binders, lubricants, inert diluents, surface active or dispersing agents. Molded tablets may be made by molding in a suitable machine, a mixture of the powdered tannins with any suitable carrier. Pharmaceutical compositions for oral administration may comprise any of the enteral nutrition compositions described above.

Compositions suitable for rectal administration may comprise a suppository, preferably bullet-shaped, containing the tannins and a pharmaceutically-acceptable carrier therefor such as hard fat, hydrogenated cocoglyceride, polyethylene glycol and the like. Compositions suitable for rectal administration may alternatively comprise the tannin and pharmaceutically-acceptable liquid carriers therefor such as 50% aqueous ethanol or an aqueous salt solution which is physiologically compatible with the rectum or colon.

In addition to the aforementioned ingredients, the compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants) and the like. For example, the tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain sucrose or fructose as a sweetening agent, methyl and propyl parabens as preservatives, a dye, and flavoring such as cherry or orange flavor. Any material used in preparing any unit dosage form should be pharmaceutically acceptable and substantially non-toxic in the amounts employed. In addition, the tannin may be incorporated into sustained-release preparations and devices.

The pharmaceutical compositions may comprise the tannin in unit dosage form. The term "unit dosage" or "unit dose" is denoted to mean a predetermined amount of the tannin sufficient to be effective for treating each of the indicated activities. Preferred unit dosage formulations are those containing a daily dose, daily sub-dose, or an appropriate fraction thereof, of the tannin. The percentage of the tannin in the pharmaceutical compositions can vary and may conveniently be from about 0.1% to about 90%, about 2% to about 60%, or about 5% to about 20%, of the weight of a given unit dosage form.

Useful dosages of the tannins described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a tannin required for use in treatment will vary not only with the particular degree of polymerization selected but also with the route of administration, the nature of the condition being treated, and the age and condition of the patient, and will be ultimately at the discretion of an attendant physician or clinician.

The tannin may be administered to the subject in an amount of from about 1 µg/kg body weight per day to about 500 mg/kg body weight per day, such as about 0.1 to about 200 mg/kg body weight per day or about 1 to about 100 mg/kg body weight per day. Specific amounts may include about 1-150, about 1-10, about 10-25, about 25-50, about 50-75, about 75-100, or about 100-150 mg tannin/kg body weight per day.

The tannin may be administered via a tube into the gastrointestinal tract that extends at least through the mouth or extends at least through the mouth and throat.

The subject to which the tannin is administered is preferably a mammal, such as a primate, human, rodent, canine, feline, bovine, ovine, equine, swine, caprine, bovine and the like.

The tannin is preferably administered to a subject receiving simplified nutrition, such as a simplified nutrition composition. The subject may be receiving such simplified nutrition during enteral or parenteral nutrition therapy. The phrase "administering to a subject receiving simplified nutrition" and variants thereof, used with respect to administering tannin, refers to administering the tannin before, during, and/or after delivery of the simplified nutrition. If the tannin is administered before delivery of the simplified nutrition, the administering preferably occurs within a timeframe such that any effects of the tannin administration overlaps with delivery of the simplified nutrition, such that any deleterious effects of the simplified nutrition are prevented or minimized. If the tannin is administered after delivery of the simplified nutrition, the administering preferably occurs within a timeframe such that any deleterious effects that do occur as a result of the simplified nutrition delivery are capable of being ameliorated. As used herein, "delivery" refers to the actual act of delivering a nutrient composition to the subject, either orally (as a solid or liquid foodstuff), enterally (via a tube through, e.g., the nasogastric system or otherwise), or parenterally (via injection or infusion into the bloodstream). The simplified nutrition composition may be administered via a tube into the gastrointestinal tract that extends at least through the mouth or that extends at least through the mouth and throat.

The administered simplified nutrition composition may comprise any enteral or parenteral nutrition composition known or used in the art. Generally, the administered simplified nutrition composition may comprise one or more of a nitrogen source, a carbohydrate source, and a lipid source.

The nitrogen source is preferably in the form of individual amino acids and/or polypeptides. Exemplary nitrogen sources include casein, caseinates, soy protein, whey protein, lactalbumin, milk protein concentrate, hydrolyzed casein, hydrolyzed soy protein, hydrolyzed whey protein, hydrolyzed lactalbumin, hydrolyzed milk protein concentrate and/or crystalline L-amino acids.

In some simplified nutrition compositions, the nitrogen source is exclusively comprised of individual amino acids or primarily comprised of individual amino acids and polypeptides having a short chain length. In various versions of the invention, for example, at least about 1% by mass, at least about 5% by mass, at least about 10% by mass, at least about 20% by mass, at least about 30% by mass, at least about 40% by mass, at least about 50% by mass, at least about 60% by mass, at least about 70% by mass, at least about 80% by mass, at least about 90% by mass, at least about 95% by mass, or at least about 99% by mass of the nitrogen source is comprised of either individual amino acids or individual amino acids in combination with polypeptides having, on average, a short chain length. As used herein, "short chain length" may refer to a chain length less than about 50 residues, less than about 40 residues, less than about 30 residues, less than about 20 residues, less than about 10 residues, less than about 5 residues, or less than about 3 residues.

If present in the simplified nutrition composition, the nitrogen source may comprise up to about 99% of the caloric content of the composition, such as about 1-99% of the caloric content of the composition, about 10-70% of the caloric content of the composition, or about 15-60% of the caloric content of the composition. Some simplified nutrition compositions may be substantially devoid of a nitrogen source, such as amino acids or polypeptides.

The carbohydrate source may comprise any combination of simple carbohydrates (i.e., monosaccharides and disaccharides) and complex carbohydrates. Exemplary carbohydrate sources include glucose, sucrose, fructose, dextrose, glucose polymers, starches such as corn starch or hydrolyzed cornstarch, dextrin, maltodextrin, and sugar alcohols.

Some simplified nutrition compositions have a high proportion of simple carbohydrates. In various versions of the invention, for example, at least about 1% by mass, at least about 5% by mass, at least about 10% by mass, at least about 20% by mass, at least about 30% by mass, at least about 40% by mass, at least about 50% by mass, at least about 60% by mass, at least about 70% by mass, at least about 80% by mass, at least about 90% by mass, at least about 95% by mass, or at least about 99% by mass of the carbohydrate source is comprised of monosaccharides or a combination of monosaccharides and disaccharides.

If present in the simplified nutrition composition, the carbohydrate source may comprise up to about 99% of the caloric content of the composition, such as about 1-99% of the caloric content of the composition, about 10-80% of the caloric content of the composition, or about 20-70% of the caloric content of the composition. Some compositions of the invention may be substantially devoid of a carbohydrate source.

The lipid source preferably comprises free fatty acids and/or glycerides (i.e., monoglycerides, diglycerides, and triglycerides). Exemplary lipid sources include fatty acid esters, fish oil, medium chain triglycerides, safflower oil, sardine oil, soybean oil, soy lecithin, structured lipids, borage oil, canola oil, corn oil, fish oil, high oleic sunflower oil, medium chain triglycerides, menhaden oil, mono- and diglycerides, palm kernel oil, safflower oil, soybean oil, soy lecithin, omega-3 fatty acids, and omega-6 fatty acids.

Some simplified nutrition compositions are low in fat with a small proportion of calories being derived from long-chain fatty acid lipids. In various versions of the invention, for example, the lipid source comprises less than about 1% by mass, less than about 5% by mass, less than about 10% by mass, less than about 20% by mass, less than about 30% by mass, less than about 40% by mass, less than about 50% by mass less than about 60% by mass, less than about 70% by mass, less than about 80% by mass, less than about 90% by mass, less than about 95% by mass, or less than about 99% by mass of long-chain fatty acid lipids. In some versions, the lipid source is substantially devoid of long-chain fatty acid lipids.

Some simplified nutrition compositions comprise medium-chain fatty acid lipids instead of long-chain fatty acid lipids. Accordingly, in various versions of the invention, at least about 1% by mass, at least about 5% by mass, at least about 10% by mass, at least about 20% by mass, at least about 30% by mass, at least about 40% by mass, at least about 50% by mass, at least about 60% by mass, at least about 70% by mass, at least about 80% by mass, at least about 90% by mass, at least about 95% by mass, or at least about 99% by mass of the lipid source is comprised of short- or medium-chain fatty acid lipids.

If present in the simplified nutrition composition, the lipid source may comprise up to about 99% of the caloric content of the composition, such as about 1-99% of the caloric content of the composition, about 10-70% of the caloric content of the composition, or about 20-60% of the caloric content of the composition. Some simplified nutrition compositions may be substantially devoid of a lipid source.

The various proportions of the nitrogen source, the carbohydrate source, and the lipid source may be adjusted based on the nutritional or medical needs of the subject. For example, some compositions may comprise about 40% of caloric content as a carbohydrate source, about 20% of caloric content as a nitrogen source, and about 40% of caloric content as a lipid source. Others may comprise about 60% of caloric content as a carbohydrate source, about 30% of caloric content as a nitrogen source, and about 20% of caloric content as a lipid source. Others may comprise about 80% of caloric content as a carbohydrate source, about 10% of caloric content as a nitrogen source, and about 10% of caloric content as a lipid source. Certain simplified nutrition compositions can contain about 17-25% of the total calories from a nitrogen source, about 35-50% of total calories from a nitrogen source, and about 25-48% of total calories from a carbohydrate source.

The caloric density of the simplified nutrition composition may have any caloric content. In some versions, the caloric content is preferably at least about 1 Kcal/mL, at least about 1.2 Kcal/mL, at least about 1.3 Kcal/mL, at least about 1.5 Kcal/mL, or about 1.3-1.5 Kcal/mL.

The administered simplified nutrition composition may comprise more than about 10%, more than about 20%, more than about 30%, more than about 30%, more than about 40%, more than about 50%, more than about 60%, more than about 70%, more than about 80%, more than about 90%, more than about 95%, more than about 99%, or about 100% of the subject's daily caloric intake. Furthermore, the subject may receive the simplified nutrition composition at such levels over a period of at least about one day, at least about two days, at least about three days, at least about 4 days, at least about 5 days, at least about 6 days, at least about 7 days, at least about two weeks, at least about three weeks, or longer.

In preferred versions of the invention, the tannin is administered to a subject receiving a simplified nutrition composition that, in the absence of tannin, results in a reduction in ileal IL-4, ileal IL-13, goblet cell density, goblet cell size, luminal MUC2 concentration, Peyer's patch lymphocytes, STAT6 phosphorylation, polymeric immunoglobulin receptor (pIgR), luminal secretory immunoglobulin-A (sIgA), and/or gut microbiota diversity in the subject. Accordingly, the tannins of the present invention are preferably administered in an amount and within a timeframe effective to counteract, minimize, or prevent such reductions. Thus, the tannins of the present invention are preferably administered in an amount and within a timeframe effective to provide a relative increase in ileal IL-4, ileal IL-13, goblet cell density, goblet cell size, luminal MUC2 concentration, Peyer's patch lymphocytes, STAT6 phosphorylation, polymeric immunoglobulin receptor (pIgR), luminal secretory immunoglobulin-A (sIgA), and/or gut microbiota diversity in the subject compared to the same subject not administered the tannins.

Additional considerations in the administration of the tannins are described by Ofman et al. Clinical economics review: nutritional support. *Ailment Pharmacol Ther* 1997, 11:453-471; and McClave et al. *Journal of Parenteral and Enteral Nutrition*, 33(3):277-316. Additional components, methods, and data are described by the doctoral thesis of Joseph Francis Pierre, "Parenteral and Elemental Enteral Nutrition Decreases Intestine Mucosal Immunity, Which is Partially Restored by Dietary Proanthocyanidins and IL-25," from University of Wisconsin—Madison; Pierre et al. *Journal of Parenteral and Enteral Nutrition*, 2013, 37(3):401-409; and Pierre J F, Heneghan A F, Feliciano R P, Shanmuganayagam D, Krueger C G, Reed J D, Kudsk K A. Cranberry Proanthocyanidins Improve Intestinal sIgA During Elemental Enteral Nutrition. *Journal of Parenteral and Enteral Nutrition*, 2013.

Examples

Abbreviations: DP, degree of polymerization; EEN, elemental enteral nutrition; GAE, gallic acid equivalents; GC, goblet cells; GALT, gut-associated lymphoid tissue; ICR, Institute of Cancer Research; JAK-STAT, Janus kinase/signal transducer and activator of transcription; MALDI-TOF MS, matrix-assisted laser desorption/ionization time-of-flight mass spectrometry; MUC2, mucin2; PAC, proanthocyanidins; PAS, periodic acid-schiff; PN, parenteral nutrition; PP, Peyer's Patch; sIgA, secretory immunoglobulin-A; pIgR, polymeric immunoglobulin receptor; Th-2, T-helper 2 lymphocytes.

Example 1. Cranberry Proanthocyanidins Attenuate the Effects of Elemental Enteral Nutrition on Size, Density and Function of Intestinal Goblet Cells in Mice Lamina propria IL-4 and IL-13 stimulate goblet cell (GC) proliferation and production of mucin 2 (MUC2) by goblet cells, which protects intestinal mucosa from bacterial pathogens. Elemental enteral nutrition (EEN) reduces IL-4 and IL-13 and impairs gut barrier function. Because cranberry proanthocyanidins (PAC) were previously shown to stimulate glycoprotein secretion in the oral cavity, we examined the effect of the addition of PAC to EEN on GC, ileal cytokines, and luminal MUC2. Male ICR mice (14 mice/group) were administered oral chow (e.g., Laboratory Rodent Diet 5001; www.labdiet.com), intragastric EEN, or intragastric EEN+PAC (8 mg (EEN+lowPAC), 50 mg (EEN+midPAC) or 100 mg (EEN+highPAC) of PAC/kg body weight) for 5 days, starting 2 days after intragastric cannulation. Ileal tissue was analyzed for IL-4, IL-13 and GC histology. Intestinal wash fluid was analyzed for MUC2. IL-4 and IL-13 were significantly lower in EEN than in the chow group. These effects were significantly attenuated in EEN+midPAC and EEN+highPAC groups. The density of GC (GC/villi), GC size and luminal MUC2 were also lower in EEN than in chow group. These effects were also significantly attenuated by the addition of PAC to EEN (EEN+midPAC and EEN+highPAC). This study indicates that the addition of cranberry PAC to EEN may counteract the impairment of barrier function of the intestinal mucosa produced by EEN by inhibiting changes in ileal IL-4 and IL-13 levels, GC density and size, and the secretion of intestinal MUC2.

This example demonstrates that the addition of physiologically relevant doses of cranberry PAC to EEN attenuates the negative effects of EEN on intestinal barrier function as determined by changes in IL-4 and IL-13, GC density and size, and luminal MUC2.

Materials and Methods.

PAC Preparation.

Non-depectinized cranberry presscake was ground with liquid nitrogen and 100 g were extracted with 400 mL of 70% acetone (Fisher Scientific, Fair Lawn, N.J.). Samples were sonicated and centrifuged at 400×g and 15° C., for 10 minutes. The extraction was repeated twice. Acetone was removed by evaporation at 35° C. and the aqueous suspension was solubilized in ethanol (Decon Labs Inc., King of Prussia, Pa.), followed by centrifugation at 13,416×g, for 10 minutes at 0° C. to eliminate ethanol insoluble material. Cranberry presscake crude extract was loaded on a Sephadex LH-20™ (GE Healthcare, Uppsala, Sweden) column that was previously swollen in water and equilibrated with ethanol for 45 minutes at 4 mL/min. Isolation of PAC was accomplished by sequential elution with ethanol, ethanol/methanol (1:1) and 80% acetone. Acetone in the last fraction that contained PAC was removed by evaporation under vacuum and the PAC was re-solubilized in methanol (Fisher Scientific, Fair Lawn, N.J.). The total phenolic content of the PAC fraction was determined by the modified Folin-Ciocalteu method (Singleton and Rossi, Amer. J. Enology and Viticulture, 1965; 16:144-58) and reported as gallic acid equivalents (GAE).

PAC Characterization by HPLC and MALDI-TOF MS.

The cranberry presscake PAC sample was diluted tenfold to reduce the amount of methanol to 10%. One hundred microliters were injected onto a Waters Spherisorb® 10 µm ODS2 RP-18 column (4.6×250 cm). The solvents for elution were trifluoroacetic acid/water (0.1%; solvent A) and methanol (solvent B). A step gradient was used, starting with 90% solvent A and 10% solvent B for 10 minutes, isocratic 72% A and 28% B between 10 and 25 minutes; a linear gradient from 28% to 55% B between 25 and 45 minutes; 45-50 minutes, a linear gradient from 55 to 99% B between 50 and 55 minutes, and isocratic 1% A and 99% B between 55 and 60 minutes. The HPLC system consisted of a Waters automated gradient controller, two Waters 501 HPLC pumps, and a Rheodyne 7125 manual injector. The flow rate was maintained at 2 mL/min, and the elution was monitored by a Waters 996 diode array detector using Waters Millennium software for collecting and analyzing three-dimensional chromatograms.

PAC characterization by matrix-assisted laser desorption/ionization time-of-flight MS (MALDI-TOF MS). The cranberry presscake PAC sample was mixed with 2,5-dihydroxybenzoic acid (Aldrich, Milwaukee, Wis.) (50 mg/mL in 100% ethanol) and the mixture was applied (1 µL) onto a MALDI-TOF MS stainless steel target and dried at room temperature. Mass spectra were collected on a Bruker Reflex II MALDI-TOF-MS (Billerica, Mass.) equipped with delayed extraction and a N2 laser (337 nm) in order to characterize the range in degree of polymerization and nature of interflavan bonds in the cranberry PAC. All preparations were analyzed in the positive ion linear and reflectron mode to detect $[M+Na]^+$ and $[M+K]^+$ molecular ions. MALDI-TOF MS is ideally suited for characterizing PAC because, unlike electrospray ionization in which multiple charge molecular ions create very complex spectral peaks that are often difficult to interpret, this mass spectral technique produces only a singly charged molecular ion for each parent molecule (Reed, Krueger, and Vestling, Phytochemistry, 2005; 66:2248-63).

Animals.

Male Institute of Cancer Research (ICR) mice were purchased through Harlan (Indianapolis, Ind.). The mice were acclimatized for one week in a temperature and humidity controlled environment with a 12 h/12 h light/dark cycle. The mice were housed 5 per microisolater-top cages and fed ad libitum chow (Rodent Diet 5001, LabDiet, PMI Nutrition International, St. Louis, Mo.) and water for 1 week prior to initiation of study protocol. Once entering study protocol, the mice were housed individually in metal wire-bottomed cages to prevent coprophagia and ingestion of bedding.

Experimental Design.

Seventy male ICR mice (6 to 8 wk old) were anesthetized with intraperitoneal administration of ketamine (100 mg/kg) and acepromazine (10 mg/kg). Gastrostomy was then performed on each mouse and the catheter was tunneled subcutaneously from the gastrostomy site, over the back, finally exiting mid-tail. The mice were partially restrained by the tail for the remainder of the study to protect the catheter during infusions (Sitren et al., *J Parenter Enteral Nutr.* 1983; 7:582-6). This partial restraint technique does not induce significant stress in the mice. The catheterized mice were connected to infusion pumps and allowed to recover for 48 hours while receiving 4 mL/d of saline (0.9%) via the catheter. The mice also received ad libitum chow (Rodent Diet 5001, LabDiet) and water.

Following the recovery period, the mice were randomized (n=14/diet group) to receive oral chow, intragastric EEN or intragastric EEN+PAC [8 mg (EEN+lowPAC), 50 mg (EEN+midPAC) or 100 mg (EEN+highPAC) GAE of PAC/kg body weight]. The chow-fed mice were given ad libitum chow and water, and continued to receive 0.9% saline at 4 mL/d via the intragastric catheter. EEN and EEN+PAC fed mice received solution at 4 mL/d (day 1), 7 mL/d (day 2) and 10 mL/d (days 3-5) as well as ad libitum water throughout the study. The EEN solution (Table 1-1) included 6% amino acids, 35.6% dextrose, electrolytes, and multivitamins, with a non-protein calorie to nitrogen ratio of 126.1 (527.0 kJ/g nitrogen). This value meets the calculated nutrient requirements of mice weighing 25 to 30 g.

TABLE 1-1

Formulation of EEN Solution.

| Component | Amount (per 1 L) | |
|---|---:|---|
| Dextrose | 356.0 | g |
| Amino acids (Clinisol) | 60.0 | g |
| Sodium chloride | 32.0 | mEq |
| Sodium phosphate | 36 | mmol |
| Potassium chloride | 16 | mEq |
| Calcium gluconate | 37.5 | mEq |
| Potassium acetate | 44.0 | mEq |
| Magnesium sulfate | 8.0 | mEq |
| Manganese | 0.8 | mg |
| Copper | 0.5 | µg |
| Zinc | 2.0 | mg |
| Vitamin C | 200 | mg |
| Vitamin A | 3300 | IU |
| Vitamin $D_3$ | 200 | IU |
| Thiamine | 6 | mg |
| Riboflavin | 3.6 | mg |
| Pyridoxine HCl | 6 | mg |
| Niacinamide | 40 | mg |
| Folic acid | 600 | mcg |
| Biotin | 60 | mcg |
| Cyanocobalamin | 5 | mcg |
| Vitamin E (dl-α-tocopheryl acetate) | 10 | IU |
| Vitamin $K_1$ | 150 | mcg |
| Dexpanthenol | 15 | mg |

After 5 d of feeding (7 days post-catheterization), mice were anesthetized as before, and exsanguinated via left axillary artery transection. The small intestine from each mouse was removed and the lumen rinsed with 20 mL HBSS (Bio Whittaker, Walkersville, Md.). The luminal rinse was centrifuged at 2,000×g for 10 minutes, and supernatant was aliquoted and frozen at −80° C. for MUC2 analysis. Ileal tissue samples were obtained from a 3 cm segment of ileum that excluded Peyer's patches. Samples for ileal IL-4 and IL-13 determination were flash-frozen in liquid N2 and stored at −80° C. until subsequent analysis, while samples for GC analysis were fixed in 4% paraformaldehyde overnight, transferred to 70% ethanol, and stored at 4° C. until subsequent histology.

Analysis of Ileal IL 4 and IL 13.

The flash-frozen small intestine segment from each animal was homogenized in RIPA lysis buffer (Upstate, Lake Placid, N.Y.) containing 1% protease inhibitor cocktail (P8340, Sigma-Aldrich, St. Louis, Mo.). The homogenate was kept on ice for 30 minutes prior to centrifugation at 16,000×g for 10 minutes at 4° C. The supernatant was then stored at −20° C. until analysis. Prior to storage, the protein concentration of the supernatant was determined by the Bradford method using BSA as a standard.

Concentrations of IL-4 and IL-13 were determined in the supernatant using solid phase sandwich ELISA kits (BD Biosciences, San Diego, Calif.), according to manufacturer's instructions. The absorbance at 450 nm was determined using a Vmax Kinetic Microplate Reader (Molecular Devices, Sunnyvale, Calif.). The IL-4 and IL-13 concentrations in the samples were determined by using a 4-parameter logistic fit standard curve (SOFTmax PRO software; Molecular Devices; Sunnyvale, Calif.) and normalized to total tissue protein content.

Analysis of Luminal MUC2.

The proteins in the intestinal wash fluid (4 μL) from each animal were separated by 10% agarose gel by electrophoresis at 150V for 80 minutes at room temperature (~23° C.). The resolved proteins were transferred to a polyvinylidene fluoride membrane using tris-glycine buffer containing 20% methanol at 80V for 60 minutes at 4° C. The membrane was blocked with 5% nonfat dry milk prepared in Tris buffered saline containing Tween (0.05%) for 1 hour at room temperature with constant agitation. Then, the membrane was incubated with mouse anti-human MUC2 (ab-11197, Abcam Inc., Cambridge, Mass.) primary antibody (diluted 1:2500) overnight at 4° C. with constant agitation. The membrane was washed and incubated with stabilized goat anti-mouse IgG-HRP conjugate (sc-2005, Santa Cruz Biotechnology, CA) secondary antibody (diluted 1:20,000) for 1 hour at room temperature with constant agitation. After washing, the membrane was incubated with HRP substrate (Super Signal West Femto substrate; Pierce, Rockford, Ill.) for 5 minutes and the protein of interest (MUC2) was detected using photographic film. The relative intensity of MUC2 for each sample was determined using NIH ImageJ software (version 1.43, http://rsbweb.nih.gov/ij/) using internal controls normalize the densitometry analysis across multiple film.

Analysis of GC Density and Size.

The fixed ileal tissue sections were processed (Tissue-Tek V.I.P, Sakura Finetek, Torrance, Calif.), and embedded in paraffin. The embedded tissue was cut (5 μm thick), deparaffinized, rehydrated through graded ethanol washes (100% ethanol×2, 95% ethanol×2, 70% ethanol×1, 2 minutes each) and placed into distilled H2O. Samples were stained with periodic acid-schiff (PAS) and counterstained with hematoxylin. GC density (GC/villi) was determined by counting taking the average number of GC present in 15 individual villi. GC size (μm2) was obtained by imaging tissue sections and analyzing individual GC with NIH ImageJ software (version 1.43, http://rsbweb.nih.gov/ij/).

Statistical Analysis.

The number of samples used from each diet group for each analysis is indicated in the corresponding figures. The significance of the differences between each diet group for each measured parameter was assessed by one-way ANOVA and the Fisher protected least significant difference (PLSD) post hoc test corrected for multiple comparisons (Statview 5.0.1, SAS, Cary, N.C.). Statistical significance was accepted at $\alpha=0.05$. Values are presented as mean±SEM.

Results.

PAC Characterization by HPLC and MALDI-TOF MS.

The cranberry presscake PAC eluted as two unresolved humps that had peak absorbance at 280 nm and minor absorbance at 520 nm due to the presence of covalently linked anthocyanin-proanthocyanidin pigments. No peaks with an absorbance max that is typical of the other classes of cranberry polyphenolic compounds (anthocyanins, hydroxycinnamic acids, and flavonols) were observed. The poorly resolved chromatogram at 280 nm reflects the large structural heterogeneity of cranberry presscake PAC (Reed, Krueger, and Vestling, Phytochemistry, 2005; 66:2248-63).

Reflectron mode MALDI-TOF MS showed masses that correspond to PAC with at least 1A-type interflavan bond in trimers to undecamers (Table 1-2). MALDI-TOF MS linear mode spectra had m/z peaks that correspond to cranberry presscake PAC with a range of 3 to 23 DP. The spectra also contained m/z peaks that correspond to covalently linked anthocyanin-proanthocyanidin molecules, ranging from monomers to heptamers (data not shown).

TABLE 1-2

Calculated and observed m/z for PAC isolated from cranberry presscake.

| | All B-type bonds | | One A-type bond | | Two A-type bonds | | Three A-type bonds | |
|---|---|---|---|---|---|---|---|---|
| | Calcd. | Obs. | Calcd. | Obs. | Calcd. | Obs. | Calcd. | Obs. |
| Trimers | 889.2 | 889.2 | 887.2 | 887.2 | 885.2 | 885.2 | | |
| Tetramers | 1177.2 | 1177.5 | 1175.2 | 1175.5 | 1173.2 | 1173.5 | 1171.2 | 1171.4 |
| Pentamers | 1465.3 | 1465.8 | 1463.3 | 1463.8 | 1461.3 | 1461.8 | 1459.3 | 1459.8 |
| Hexamers | 1753.3 | 1754.0 | 1751.3 | 1752.0 | 1749.3 | 1749.9 | 1747.3 | 1748.2 |
| Heptamers | 2041.4 | 2042.3 | 2039.4 | 2040.3 | 2037.4 | 2038.3 | 2035.4 | 2036.4 |
| Octamers | 2329.5 | 2330.4 | 2327.4 | 2328.7 | 2325.4 | 2326.6 | 2323.4 | 2324.7 |
| Nonamers | 2617.6 | 2618.9 | 2615.6 | 2617.0 | 2613.5 | 2615.0 | 2611.5 | 2613.2 |
| Decamers | 2905.6 | 2906.2 | 2903.5 | 2904.1 | 2901.5 | 2902.0 | 2899.5 | 2900.7 |
| Undecamers | | | 3191.7 | 3192.4 | 3189.7 | 3190.3 | 3187.6 | 3188.9 |

The observed masses were determined by MALDI-TOF MS and the calculated masses were based on m/z=290+288d−2A+c, where 290 represents the molecular weight of the terminal catechin/epicatechin unit, d is the degree of polymerization, A is the number of A-type interflavan bonds and c is the molecular weight of sodium cations. Blank spaces indicate that a mass was not observed (signal to noise ratio <3.0).

Analysis of Ileal IL-4 and IL-13.

Figure 1:
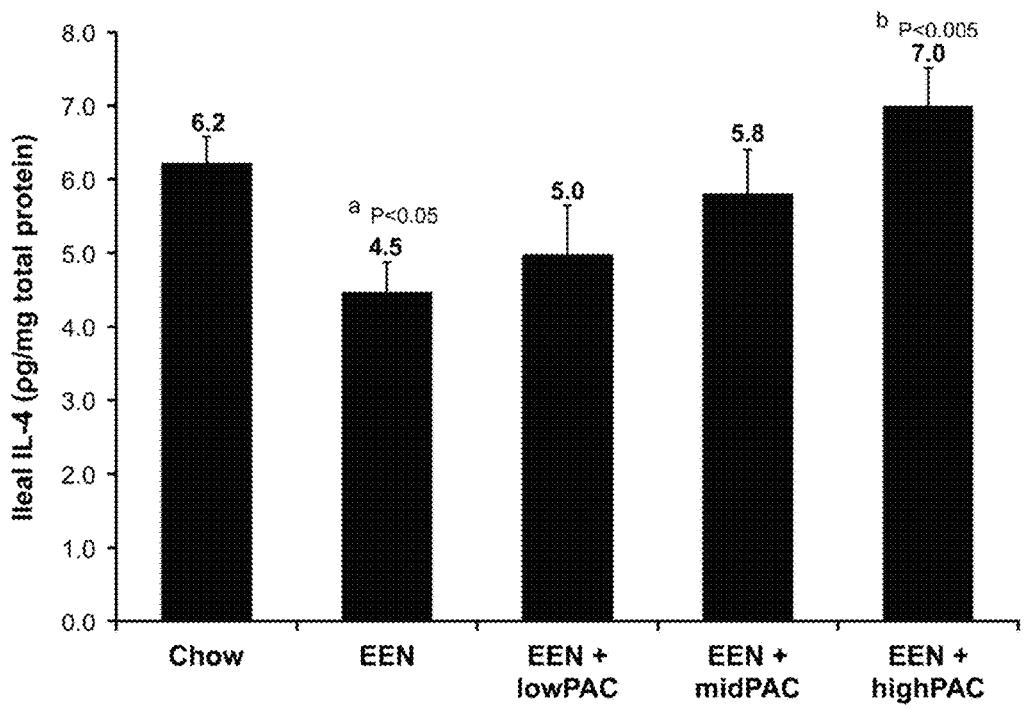
FIG. 1 depicts the effect of chow (n=11), elementary enteral nutrition (EEN) (n=14), EEN+low proanthocyanidin (lowPAC; 8 mg gallic acid equivalents of PAC/kg body weight) (n=14), EEN+mid proanthocyanidin (midPAC; 50 mg gallic acid equivalents of PAC/kg body weight) (n=14), and EEN+high proanthocyanidin (highPAC; 100 mg gallic acid equivalents of PAC/kg body weight) (n=14) feeding on ileal tissue IL-4 levels.
Figure 2:
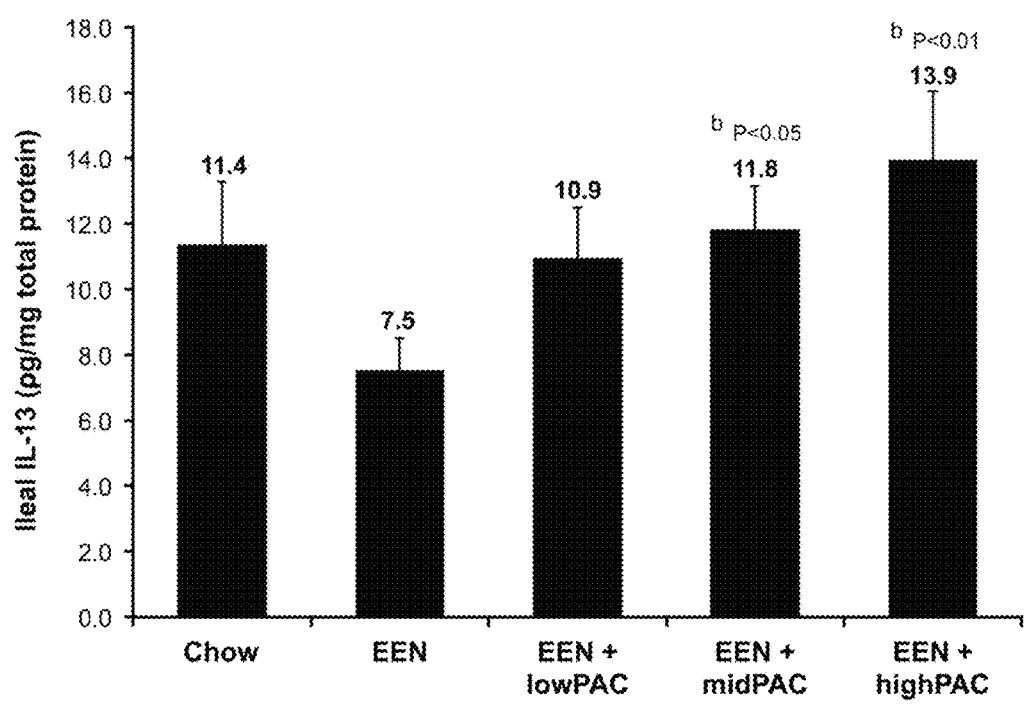
FIG. 2 depicts the effect of chow (n=6), EEN (n=8), EEN+lowPAC (n=8), EEN+midPAC (n=8), and EEN+highPAC (n=5) feeding on ileal tissue IL-13 levels.
Figure 3:
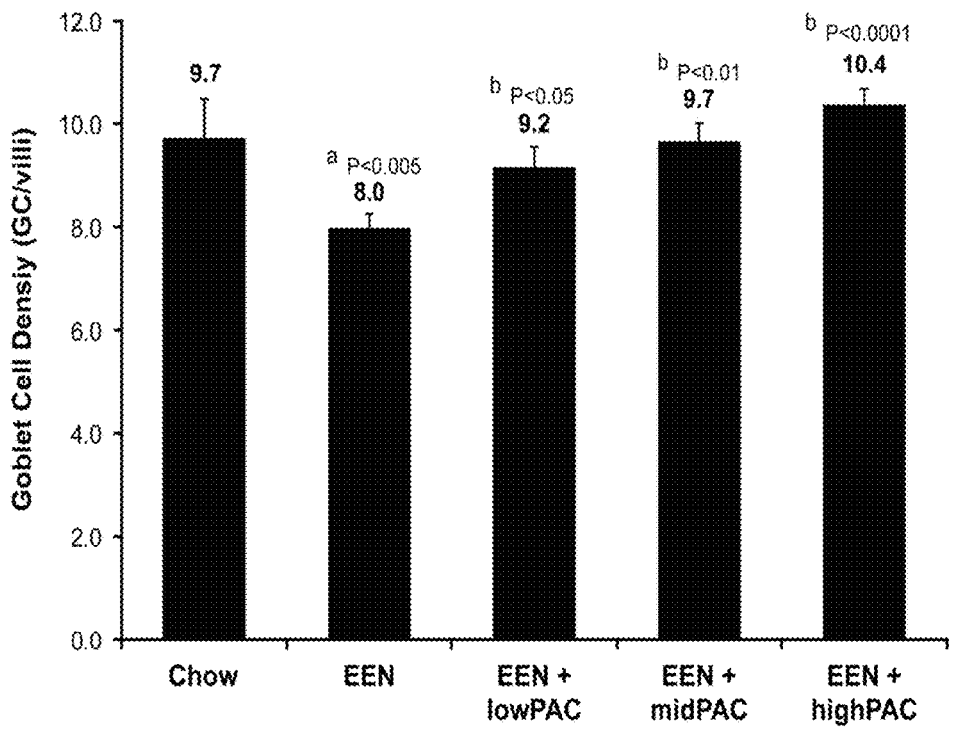
FIG. 3 depicts the effect of chow (n=8), EEN (n=12), EEN+lowPAC (n=8), EEN+midPAC (n=7), and EEN+highPAC (n=10) feeding on ileal goblet cell density.

IL-4 level in the ileal tissue of the EEN group (4.5±0.4 pg/mg total protein) was significantly lower than in the chow group (6.2±0.4, P<0.05) (FIG. 1). IL-4 level in the EEN+highPAC group (7.0±0.5) was significantly higher than in the EEN group (P<0.005), while neither the levels in EEN+lowPAC (5.0±0.7) nor EEN+midPAC (5.8±0.6) groups significantly differed from that in the EEN group.

Although IL-13 in the ileal tissue was significantly lower in the EEN group (7.5±1.0 pg/mg total protein) than in the chow group (11.4±1.9) (FIG. 2), the difference did not reach statistical significance (P=0.08). IL-13 in the EEN+midPAC (11.8±1.3, P<0.05) and EEN+highPAC (13.9±2.1, P<0.01) were significantly higher than in the EEN group.

Analysis of GC Density and Size.

The density of GC (FIG. 3) in the EEN group (8.0±0.3 GC/villi) was significantly lower than in the chow group (9.7±0.7, P<0.005). The GC density in the EEN+lowPAC (9.2±0.4, P<0.05), EEN+midPAC (9.7±0.4, P<0.01), and EEN+highPAC (10.4±0.3, P<0.0001) groups were significantly higher than in the EEN group. The GC density in the EEN+highPAC group was also significantly greater than in the EEN+lowPAC group (P<0.05).

Figure 4:
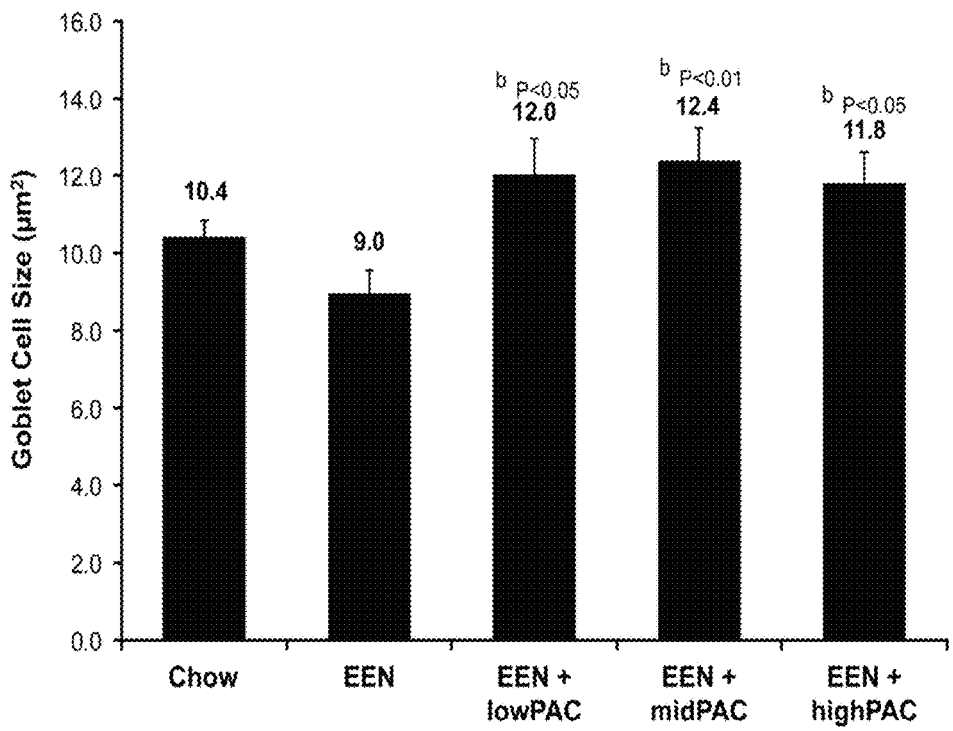
FIG. 4 depicts the effect of chow (n=6), EEN (n=7), EEN+lowPAC (n=6), EEN+midPAC (n=8), and EEN+highPAC (n=7) feeding on ileal goblet cell size.

Although the GC size in the EEN group (9.0±0.6 µm2) was smaller than in the chow group (10.4±0.4), the difference did not reach statistical significance (P=0.23) (FIG. 4). The GC sizes in the EEN+lowPAC (12.0±0.9, P<0.01), EEN+midPAC (12.4±0.9, P<0.01), and EEN+highPAC (11.8±0.8, P<0.05) groups were significantly greater than in the EEN group.

Analysis of Luminal MUC2.

Figure 5:
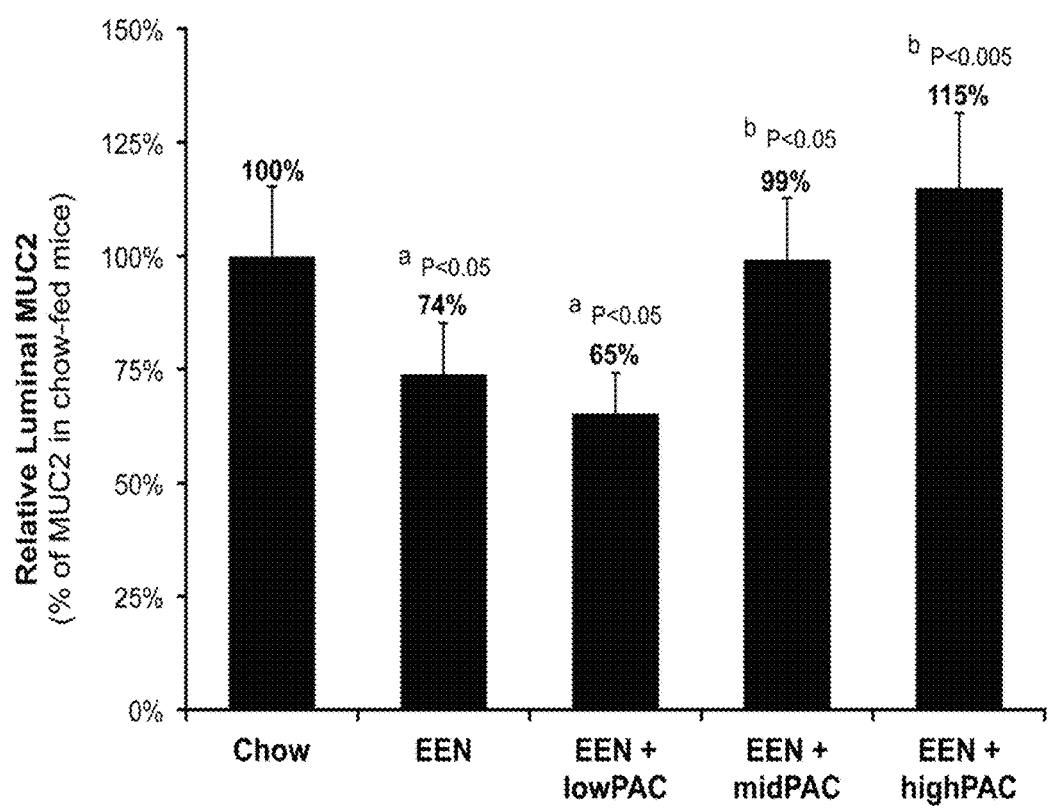
FIG. 5 depicts the effect of chow (n=9), EEN (n=10), EEN+lowPAC (n=7), EEN+midPAC (n=9), and EEN+highPAC (n=8) feeding on luminal MUC2.

The relative luminal MUC2 within the small intestine in the EEN (75±11% of chow group, P<0.05) and EEN+lowPAC (65±9% of chow group, P<0.05) groups were significantly lower in the chow group (FIG. 5). However, the relative luminal MUC2 in the EEN+midPAC (99±14% of chow group, P<0.05) and EEN+highPAC (115±16% of chow group, P<0.005) groups were significantly higher than in the EEN group.

Discussion.

A major finding of this example is that the addition of cranberry PAC to EEN solution attenuates the effects of EEN on ileal tissue IL-4 and IL-13 levels, GC density and size, and the secretion of intestinal MUC2. Reduced ileal tissue IL-4 and IL-13 levels, GC density and size, and secretion of intestinal MUC2 contributes to the impairment of the mucosal barrier integrity observed in conjunction with EEN therapy.

PAC are complex oligomeric polyphenolic compounds widely distributed in fruits, including grapes, cranberries, and apples, and other foods and beverages such as chocolate and wine. Epidemiological studies suggest PAC may have beneficial health effects. However, PAC are minimally absorbed across the enterocyte layer due to non-hydrolyzable bonds between flavan-3-ol monomeric units and their ability to complex both dietary and endogenous proteins. Further, PAC oligomers range in DP from 3 to 30, or more, and therefore have higher molecular weight than other common plant polyphenols. Consequentially, greater than 95% of PAC remain in the intestinal lumen during transit through the gastrointestinal tract.

While PAC are poorly absorbed, they can provide several beneficial effects. PAC can exert antioxidant and non-specific antimicrobial functions within the gut, and the addition of dietary PAC can palliate chemically-induced colitis. PAC can also complex salivary glycoproteins when ingested, a process that causes the astringency of many fruits and beverages. Astringency occurs when PAC crosslink and precipitate salivary glycoproteins. PAC with higher DP have greater effects on crosslinking and precipitation. Several biological effects occur in response to astringency including increased salivary excretion, hypertrophy of the parotid gland, and shift in salivary composition to proline rich proteins. In response to PAC within the intestine, intraepithelial γδ T lymphocytes activate and proliferate. Interestingly, the level of γδ T cell response also increases with greater DP of PAC. This indicates that PAC can improve mucosal barrier physiology and immunity, and that an increased DP of PAC can provide additional benefits.

The cranberry presscake PAC was first analyzed by HPLC to confirm that the preparation did not contain other classes of cranberry phenolic compounds. A MALDI-TOF MS technique that is capable of determining the structural complexity of PAC was used to estimate the range in DP and elucidate PAC structural features (Reed, Krueger, and Vestling, Phytochemistry, 2005; 66:2248-63; Hanton, Chem. Rev. 2001; 101:527-69; Krueger, Vestling, Reed, J. Agric. Food Chem. 2003; 51:538-43). Both linear and reflectron modes were used in this work because they provide complimentary information. High resolution was achieved in the reflectron mode while high sensitivity was obtained in the linear mode, particularly at high molecular weight samples.

The cranberry presscake PAC oligomers detected in this example in reflectron mode are consistent with other work in which PAC ranging from tetramers to tridecamers were detected (White et al., J. Agric. Food Chem. 2010; 58:4030-6). Higher resolution of reflectron mode spectra allowed detection of overlapping isotope patterns due to the presence of PAC with 1, 2 and 3A-type linkages that are 2 amu apart (Table 1-2), as previously reported (Neto et al., J. Sci. Food Agric. 2006; 86:18-25; Porter et al., J. Sci. Food Agric. 2001; 81:1306-13). Linear mode MALDI-TOF MS detected oligomers with a DP of 23 flavan units. Although the cranberry presscake PAC preparation is a complex mixture of closely related oligomers, detailed analysis by HPLC and MALDI-TOF MS allowed for the characterization and reliable reproduction of chromatographic fractions for inclusion in experimental diets.

In this example, investigations evaluated the effects of addition of cranberry PAC to EEN solution on ileal tissue IL-4 and IL-13 levels, GC density and size, and the secretion of the primary glycoprotein MUC2, and explored the effect of physiological doses of PAC on these parameters. A chemically-defined EEN solution administered via a gastrostomy tube was used as a model of an elemental enteral diet (Li et al., J. Trauma 1995; 39:44-51). The EEN administration results in reproducible effects on intestinal (and respiratory) mucosal immunity allowing examination of changes induced with PAC. While the lower GC size observed with EEN compared to chow were not statistically significant level, the data demonstrate that EEN produces significantly lower density of ileal GC compared to chow feeding. Since GC differentiate, migrate up the villi, and slough off every 3-5 days, these findings indicate that reduced dietary complexity alters the rate of cellular differentiation of progenitor crypt stem cells to GC, likely via changes in Th-2 type cytokines observed with EEN.

Goblet cells normally undergo hypertrophy and hyperplasia in response to IL-4 and IL-13, which act through the IL-4 receptor a and IL-13 receptor a1, respectively. The data presented herein shows that EEN lowers ileal IL-4 and IL-13 levels. Simultaneously, EEN significantly decreases the concentration of MUC2 within the lumen. Functionally, MUC2 forms the viscous mucin layer that overlays the intestinal surface, allowing smooth passage of digesta. From an immunological stand point, secreted antimicrobial proteins and peptides from Paneth cells as well as secretory IgA (sIgA) localize and are concentrated in this layer. These mucin glycoproteins also provide endogenous flora under a consistent nutrient source. The observed decrease in luminal MUC2 likely increases susceptibility to bacterial opportunistic pathogens or intestinal inflammation, which effect is supported by findings of others showing that MUC2−/− mice are at increased risk for spontaneous colitis (Bergstrom et al., PLoS Pathog. 2010; 6:e1000902).

Overall, this example shows that reduced enteral stimulation results in the impairment of mucosal integrity and gut barrier function through the reduction in the mucin component. This example demonstrates that the administration of EEN produces lower levels of Th2 stimulating cytokines, IL-4 and IL-13, lower GC density and size, and lower luminal MUC2 levels in the ileum. The addition of cranberry PAC to this diet, at physiologic doses, attenuates these changes and normalizes mucosal integrity. This indicates that a non-nutritional dietary component such as PAC can influence health without being absorbed from the gastrointestinal tract, thereby providing a significant benefit when used in conjunction with a restricted diet such as elemental enteral nutrition.

Example 2. Cranberry Proanthocyanidins Improve Intestinal sIgA During Elemental Enteral Nutrition Elemental enteral nutrition (EEN) decreases gut-associated lymphoid tissue (GALT) function, including fewer Peyer's patch lymphocytes, lower levels of the tissue Th2 cytokines and mucosal transport protein polymeric immunoglobulin receptor (pIgR), leading to lower luminal sIgA levels. Example 1 above demonstrates that cranberry proanthocyanidins (PAC) maintain the Th2 cytokine IL-4 when added to EEN. This example shows that the addition of PAC to EEN normalizes other GALT parameters and maintains luminal levels of sIgA.

Briefly, ICR mice were randomized (12/group) to receive Chow, EEN, or EEN+PAC (100 mg/kg body weight) for 5 days, starting 2 days after intra-gastric cannulation. Ileum tissue was collected to measure IL-4 by ELISA, pIgR by western blot, and phosphorylated STAT6 by microarray. Intestinal wash fluid was collected to measure sIgA by western blot. Compared with Chow, EEN significantly decreased tissue IL-4, phosphorylated STAT6, and pIgR. The addition of PAC to EEN prevented these alterations. Compared with Chow, EEN resulted in significantly lower levels of luminal sIgA. The addition of PAC to EEN increased luminal sIgA levels compared to EEN alone. Therefore, the addition of PAC to EEN can support GALT function and maintain intestinal sIgA levels compared with EEN alimentation alone.

Decreased dietary bulk and complexity provided with EEN attenuates mucosal agitation and painful symptoms. Unfortunately, reduced dietary complexity, such as provided with EEN or parenteral nutrition (PN), alters the structure and function of the gut-associated lymphoid tissue (GALT). Ultimately, reduced dietary complexity manifests as decreased secretory immunoglobulin-A (sIgA) in the gut lumen compared to enteral feeds. sIgA is the primary protective compound of acquired immunity secreted by the host mucosa, which among other notable functions exclude enteric bacteria from attachment to the host. EEN also results in increased bacterial translocation and decreased microbiome diversity. To address EEN-induced susceptibilities, various interventions have been investigated to provide anti-inflammatory and protective effects in the gut. An established feeding model employing intra-gastric administered EEN results in the reproducible loss of intestinal (and respiratory) sIgA. This example evaluated whether a class of natural compounds isolated from cranberries, proanthocyanidins (PAC), support mucosal protection by stimulating luminal sIgA levels when added to EEN.

Reduced luminal sIgA levels following EEN or parenteral nutrition is multifactorial, including fewer lymphocyte numbers in both Peyer's patches (PP) and lamina propria compartments; suppressed T helper 2 (Th2) cytokines, IL-4 and IL-10, in the lamina propria; and reduced expression of mucosal pIgR, which is the primary transport protein for sIgA. Expression of pIgR is regulated in part through the Janus kinase/signal transducer and activator of transcription (JAK/STAT) pathway, a cytokine signaling cascade used to transduce a wide array of cellular events. IL-4 binds the IL-4 receptor-α inducing intracellular STAT6-phosphoyrlation, dimerization, and migration into the cell nucleus targeting transcription products, including pIgR. EEN decreases sIgA levels and PAC support intestinal Th2 cytokines. Additionally, it was found that the addition of physiological PAC doses to EEN supports GALT function and luminal sIgA compared with EEN alimentation alone.

PAC preparation and characterization was carried out as described in Example 1. Mice were obtained and acclimatized as described in Example 1.

Experimental Design.

Male ICR mice, ages 6 to 8 weeks, were randomized to Chow with a gastric catheter (n=12), intragastric elemental nutrition (EEN) (n=12) via gastrostomy, or EEN+PAC via gastrostomy (100 mg/kg body weight (EEN+PAC)) (n=12). Animals were anesthetized by intraperitoneal injection of ketamine (100 mg/kg) and acepromazine (10 mg/kg). Catheters were tunneled subcutaneously from the gastrostomy site over the back and exited mid tail. Mice were partially immobilized by tail fixation to protect the catheter during infusion. This technique does not induce significant physical or biochemical stress.

Catherized mice were connected to infusion pumps and allowed recovery for 48 hours while receiving 4 mL/day saline (0.9%) and ad libitum chow (Agway Inc., Syracuse, N.Y.) and water. Following the recovery period experimental diets were given. Chow mice continued to receive 0.9% saline at 4 mL/day as well as ad libitum chow and water throughout the study. The EEN solution includes 6% amino acids, 35.6% dextrose, electrolytes, and multivitamins, with a non-protein calorie/nitrogen ratio of 126.1 (527.0 kJ/g Nitrogen). This value meets the calculated nutrient requirements of mice weighing 25 to 30 g. EEN and EEN+PAC fed mice received solution at 4 mL/day (day 1), 7 mL/day (day 2) and 10 mL/day (days 3-5) as well as ad libitum water throughout the study.

After 5 days of feeding (7 days post-catherterization), mice were anesthetized by intraperitoneal injection of ketamine (100 mg/kg) and acepromazine (10 mg/kg), and exsanguinated via left axillary artery transection. The small intestine was removed and the lumen rinsed with 20 mL Hanks Balanced Saline Solution (HBSS, Bio Whittaker, Walkersville, Md.). The luminal rinse was centrifuged at 2,000×g for 10 min and supernatant aliquots were frozen at −80° C. for sIgA analysis. Tissue samples were taken by removing a 3 cm segment of ileum excluding PPs. PP lymphocytes were assessed by counting on a hemocytometer. Samples were frozen in liquid N2 and stored at −80° C. until processing or fixed in 4% paraformaldehyde overnight, transferred to 70% ethanol, and stored at 4° C. for immunohistochemistry.

Peyer's Patch Lymphocytes.

The Peyer's patch (PP) from the entire length of the SI was removed into 1.5 mL tubes of CMF-HBSS. PP were strained through 100-µm mesh with a total volume of 15 mL CMF-HBSS. The effluent was collected and spun at 1700 rpm at 5° C. for 10 min. The supernatant was removed and the pellet resuspended in 15 mL CMF-HBSS; this step was repeated. Cells were counted on a hemocytometer with trypan blue.

Tissue Cytokine Quantitative Analysis.

The flash-frozen small intestine segment from each animal was homogenized in RIM lysis buffer (Upstate, Lake Placid, N.Y.) containing 1% protease inhibitor cocktail (P8340, Sigma-Aldrich, St. Louis, Mo.). The homogenate was kept on ice for 30 minutes prior to centrifugation at 16,000×g for 10 minutes at 4° C. The supernatant was then stored at −20° C. until analysis. Prior to storage, the protein concentration of the supernatant was determined by the Bradford method using BSA as a standard.

Concentration of IL-4 was determined in the supernatant using solid phase sandwich ELISA kits (BD Biosciences, San Diego, Calif.), according to manufacturer's instructions. The absorbance at 450 nm was determined using a Vmax Kinetic Microplate Reader (Molecular Devices, Sunnyvale, Calif.). The IL-4 concentrations in the samples were determined by using a 4-parameter logistic fit standard curve (SOFTmax PRO software; Molecular Devices; Sunnyvale, Calif.) and normalized to total tissue protein content.

JAK-STAT Profiling by the JAK-STAT Antibody Microarray.

The Phospho Explorer antibody microarray (Full Moon Biosystems Inc., Sunnyvale, Calif.), contains 42 antibodies. Each of the antibodies has six replicates that are printed on coated glass microscope slide, along with multiple positive and negative controls. The antibody array experiment was performed according to established protocol (Kang et al., J. Clin. Invest. 2010, 120, 1165-1177). In brief, ileum tissue lysates (n=8/group) were biotinylated with Antibody Array Assay Kit. The antibody microarray slides were first blocked in a blocking solution for 30 minutes at room temperature, rinsed with Milli-Q grade water for 5 minutes, and dried with compressed nitrogen. The slides were then incubated with the biotin-labeled cell lysates (~80 µg protein) in coupling solution at room temperature for 2 hours. The array slides were washed 5 times with 1× Wash Solution and rinsed extensively with Milli-Q grade water before detection of bound biotinylated proteins using Cy3-conjugated streptavidin. The slides were scanned on a GenePix 4000 scanner and the images were analyzed with GenePix Pro 6.0 (Molecular Devices, Sunnyvale, Calif.). The fluorescence signal of each antibody was obtained from the fluorescence intensity of this antibody spot after subtraction of the blank signal (spot in the absence of antibody), and the signal of the phosphorylated protein to GAPDH housekeeping protein expression was used.

Analysis of pIgR Expression by Western Blot.

Solubilized protein from small intestinal tissue homogenate was denatured at 95° C. for 10 minutes with sodium dodecylsulfate and β-mercaptoethanol, and 20 µg of protein from each sample was separated in a denaturing 10% polyacrylamide gel by electrophoresis at 150V for 1 hour at room temperature. Proteins were transferred to a PVDF membrane, and western blot was performed as previously described (Sano et al., Am. J. Surg. 2009, 198, 105-109). Densitometric measurements of protein bands were analyzed and quantified with the NIH Image J software. pIgR standard (Cat 2800, R&D, Minneapolis, Minn.) was used to compare multiple gels. The combined value of the 120 kDa and 94 kDa bands was determined for the quantitation of the pIgR protein expression in sample.

Analysis of IgA by Western Blot.

Luminal wash IgA was measured by western blot because it was observed that the addition of PAC to control animal luminal wash samples rapidly decreases sensitivity and total signal measured by IgA ELISA (unpublished observation), likely through the complexation between PAC with proteins. Four µL of luminal fluid was denatured at 95° C. for 10 minutes with sodium dodecylsulfate and β-mercaptoethanol. Proteins were separated in a denaturing 10% polyacrylamide gel by electrophoresis at 150 V for 1 hour at room temperature and transferred to a polyvinylidene fluoride membrane using tris-glycine buffer plus 20% methanol at 80 V for 50 minutes at 4° C. The membrane was blocked with 5% nonfat dry milk prepared in TBS-Tween for 1 hour at room temperature with constant agitation. Membranes were incubated with goat anti-mouse IgA, α-chain specific (Sigma-Aldrich, St. Louis, Mo.) diluted 1:7,000 for 1 hour at room temperature with constant agitation. Then, membranes were washed and incubated with stabilized donkey anti-goat IgA-HRP conjugated secondary diluted 1:20,000 for 1 hour at room temperature. After washing, membranes were incubated with HRP substrate (Super Signal West Femto maximum sensitivity substrate; Pierce, Rockford, Ill.) for 5 minutes and bands were detected using photographic film. Densitometric measurements of immunoglobulin α-chain protein bands (~55 kDa) were analyzed and quantified with the NIH Image J software. IgA heavy chain standard (M-1421, Sigma-Aldrich) was used to normalize across multiple gels.

Statistical Analysis.

Experimental values were compared using analysis of variance (ANOVA) and Fisher protected least significance difference (PLSD) corrected for multiple comparisons, with $\alpha=0.05$ considered significant (Statview 5.0.1, SAS, Cary, N.C.). Numerical results are presented as mean±standard deviation of the mean.

Results.

PAC Characterization by HPLC and MALDI-TOF MS.

The cranberry presscake PAC eluted as two unresolved peaks that had absorbance at 280 nm and minor absorbance at 520 nm due to the presence of covalently linked anthocyanin-proanthocyanidin pigments. No peaks were observed with an absorbance max typical of the other classes of cranberry polyphenolic compounds (anthocyanins, hydroxycinnamic acids, and flavonols). The poorly resolved chromatogram at 280 nm is due to structural heterogeneity of cranberry presscake PAC.

Reflectron mode MALDI-TOF MS showed masses that correspond to PAC with at least 1 A-type interflavan bond in trimers to undecamers. MALDI-TOF MS linear mode spectra had m/z peaks that correspond to cranberry presscake PAC with a range of 3 to 23 degrees of polymerization. The spectra also contained m/z peaks that correspond to covalently linked anthocyanin-proanthocyanidin molecules, ranging from monomers to heptamers (data not shown).

Peyer's Patch Lymphocytes.

Compared with Chow (4.533×106±1.226×106 cells), EEN significantly lowered PP lymphocytes (2.428× 106±0.574×106 cells, P<0.0001) (FIG. 6). Compared with EEN alone, PP lymphocytes were significantly higher in EEN+PAC ($3.957 \times 10^6 \pm 1.291 \times 10^6$ cells, P<0.001). There were no significant differences between Chow and EEN+PAC (P=0.19).

Ileum Tissue IL-4.

Compared with Chow (6.5±1.11 pg/mg protein), EEN significantly lowered ileum IL-4 (4.15±1.44, P<0.01) (FIG. 7). Compared with EEN alone, ileum IL-4 was significantly higher in EEN+PAC (5.8±2.2, P<0.05). There was no significant difference between the level of ileum IL-4 between Chow and EEN+PAC (P=0.42).

Ileum Tissue Phosphorylated STAT6.

Phosphorylated STAT6 (PSTAT6) was measured at two phosphorylation sites, Tyrosine 641 (Tyr641) and Threonine 645 (Thr645), and normalized to GAPDH expression. Compared with Chow (8.66±1.5 PSTAT6 (Tyr641)/GAPDH), PSTAT6 at Tyr641 site was significantly reduced with EEN (6.08±1.3, P<0.001). The addition of PAC to EEN significantly elevated PSTAT6 at Tyr 641 (8.11±0.7, P<0.01). There was no difference between Chow and EEN+PAC (P=0.37) (FIG. 8A). Similarly, compared with Chow (8.97±1.6 PSTAT6 (Thr645)/GAPDH), PSTAT6 at Thr645 was significantly lower with EEN (6.60±1.0, P<0.01). The addition of PAC to EEN significantly elevated PSTAT6 at Thr645 (7.99±0.9, P<0.05), however, there was no significant difference between Chow and EEN+PAC (P=0.13) (FIG. 8B).

Ileum Tissue pIgR.

EEN (10.23±5.23) lowered tissue pIgR (relative concentration/20 μg protein) compared with Chow (20.71±7.63, P<0.001) (FIG. 9). PAC+EEN (16.13±5.97, P<0.03) levels of tissue pIgR were significantly higher than EEN alone. There was no significant difference between Chow and EEN+PAC (P=0.08).

Luminal sIgA.

Compared with Chow (17.62±6.52), the level of luminal sIgA (relative concentration/4 μL luminal wash) was significantly lower following EEN (10.33±4.23, P<0.001) (FIG. 10). The addition of PAC to EEN (14.67±5.86, P<0.05) significantly elevated luminal sIgA compared with EEN alone. There was no significant difference between EEN+PAC and Chow (P=0.15).

Discussion.

EEN allows alimentation to patients with contraindication to normal feeding by administering a liquid diet directly into the gastrointestinal tract. EEN formulas are usually used in clinical conditions involving intestinal or pancreatic inflammation. The administration of a glucose-amino acid infusion (EEN) administered via gastrostomy decreases several aspects of GALT function, including fewer PP and lamina propria lymphocytes; reduced tissue IL-4 and IL-10; pIgR, the sIgA mucosal transport protein; and decreased levels of luminal sIgA. Unfortunately, these changes result in increased susceptibility to infection and inflammation because sIgA is the primary protective molecule of specific (acquired) immunity that is secreted onto mucosal surfaces. sIgA opsinizes bacteria, preventing their attachment to the mucosa, and reduces virulent expression in enteric pathogens. Consistent with its negative effect on luminal sIgA, EEN also increases mucosal barrier permeability and decreases microbiome diversity. Because EEN is the only enteral formula tolerated in certain patients, EEN supplements that improve host immune and barrier function are of particular value. In this example, the effect of PAC upon GALT function was investigated. The PAC led to the release of sIgA in the intestinal lumen.

PAC are complex oligomeric polyphenolic compounds distributed in fruits, including grapes, cranberries, and apples, and other foods and beverages such as chocolate and wine. PAC do not appear to leave the gut lumen for a variety of reasons, including non-hydrolysable bonds between flavan-3-ol monomeric units and their ability to complex both dietary and endogenous proteins. Further, PAC oligomers range in degree of polymerization from 3 to 25+ and therefore have higher molecular weight than other common plant polyphenols. Due to these characteristics, rodent models demonstrate greater than 95% of PAC remain in the intestinal lumen during transit through the gastrointestinal tract, and ingested PAC do not contribute to circulating flavanol levels in humans. PAC can therefore exert beneficial health effects through their interaction at the gut mucosa.

The expression of pIgR is regulated through IL-4 stimulation of the nuclear factor STAT-6, a member of the JAK/STAT signaling cascade. STAT-6, in part, regulates luminal sIgA through regulation of the mucosal transport protein pIgR. The importance of STAT-6 during parenteral nutrition with lack of enteral stimulation has been established, showing that lower IL-4 levels correlated levels of phosphorylated STAT-6, pIgR, and luminal sIgA. Administration of exogenous cytokines that stimulate STAT-6 phosphorylation during parenteral nutrition significantly increased levels of pIgR expression and luminal IgA levels, indicating a cause and effect relationship. In this example, EEN decreased intestinal tissue levels of IL-4 and phosphorylated STAT-6, correlated with decreased pIgR and luminal sIgA. The addition of PAC to EEN at physiological levels (100 mg GAE/kg body weight) resulted in increased tissue IL-4, STAT-6 phosphorylation, pIgR, and luminal sIgA, supporting that PAC can influence health by interacting with GALT function.

This is the first study to demonstrate that PAC supplementation can improve luminal sIgA during EEN. PAC posed a significant challenge for accurately quantifying luminal sIgA, because PAC form complexation with endogenous and dietary proteins, including immunoglobulins, through hydrophobic and hydrogen bonding interaction. During analysis it was observed that the addition of small concentrations of PAC to luminal wash fluid from control animals rapidly decreased the detectable levels of sIgA via ELISA quantification (unpublished observation). For this reason, measurement of luminal sIgA in this study was achieved by first denaturing and reducing intestinal wash fluid samples with heat, sodium dodecyl sulfate, and β-mercaptoethanol and performing western blot analysis to detect the sIgA heavy chain directly. Future work with PAC should take the complexation and masking effect into consideration when investigating intestinal sIgA.

In summary, this example shows that decreased enteral stimulation, such as EEN or parenteral feeding, suppresses GALT function—including total PP and lamina propria lymphocytes numbers, Th2 cytokine levels, and the mucosal sIgA transport protein, pIgR—that leads to reduced luminal sIgA levels. Consistent with the concept that PAC can provide immunoprotective effects through interactions with the GALT and intestinal mucosa, the supplementation of physiological doses of PAC to EEN elevated GALT function and luminal sIgA compared to EEN feeding alone. This example indicates that moderate levels of PAC are beneficial when added to enteral diets by promotion of adaptive immune function.

Example 3. Enteral Proanthocyanidin Formulation

A liquid enteral formulation can be prepared to include proanthocyanidins (1 μg/kg to 100 mg/kg; or about 8-100 mg/kg of patient body weight; higher order polymers of PAC can be effective at lower dosage ranges) and protein at about 25% of total calories by including about 87% of the protein from partially hydrolyzed casein and about 13% from one or more of the free amino acids arginine, cysteine, glutamine, ornithine, and proline. Carbohydrates can be included at about 35-40% of calories. Lipids can be added to comprise about 38-42% of calories, for example, as a blend of medium chain triglycerides (50%), fish oil (25%), soy oil and/or soy lecithin (25%). Vitamin and mineral content can be formulated to meet daily requirements for a diet designed to provide approximately 1500 calories (e.g., with approximately 1000 mL of the formulation). The proportions of the formulation can be adjusted higher for increased caloric needs.

Example 4. Examples of Parenteral Nutrition Formulations

The tannins described herein can be added to enteral nutrition formulations such as that summarized in Table 4-2. The formulation can be varied by adding triglycerides, e.g., including omega 3 and omega-6 fatty acids, formulated to be administered in a parenteral nutrition formulation. Vitamins and minerals included in the multivitamin infusion can include the ingredients described by Li et. al in "Effects of parenteral and enteral nutrition on gut-associated lymphoid tissue"; J. Trauma 1995; 39:44-51 at Table 2. An exemplary parenteral formulation is shown in Table 4-1.

TABLE 4-1

Formulation of a parenteral nutrition solution (per 1 L).

| Component | Amount |
|---|---|
| Glucose | 340 g |
| Amino acids | 44.7 g |
| Sodium chloride | 32 mEq |
| Sodium phosphate | 36 mmol |
| Potassium chloride | 16 mEq |
| Calcium gluconate | 37.5 mEq |
| Potassium acetate | 144 mEq |
| Magnesium sulfate | 8 mEq |
| Manganese | 0.8 mg |
| Copper | 0.5 μg |
| Zinc | 2 mg |
| Multivitamin infusion | 10 mL |

TABLE 4-2

Formulation of an elemental enteral nutrition solution (per 1 L).

| Component | Amount |
|---|---|
| Glucose | 356 g |
| Amino acids (Clinisol) | 60 g |
| Sodium chloride | 32 mEq |
| Sodium phosphate | 36 mmol |
| Potassium chloride | 16 mEq |
| Calcium gluconate | 37.5 mEq |
| Potassium acetate | 44 mEq |
| Magnesium sulfate | 8 mEq |
| Manganese | 0.8 mg |
| Copper | 0.5 μg |
| Zinc | 2.0 mg |
| Vitamin C | 200 mg |
| Vitamin A | 3300 IU |
| Vitamin $D_3$ | 200 IU |
| Thiamine | 6 mg |
| Riboflavan | 3.6 mg |
| Pyridoxine HCl | 6 mg |

TABLE 4-2-continued

Formulation of an elemental enteral nutrition solution (per 1 L).

| Component | Amount |
|---|---|
| Niacinamide | 40 mg |
| Folic Acid | 600 mcg |
| Biotin | 60 mcg |
| Cyanocobalamin | 5 mcg |
| Vitamin E (dl-α-tocopheryl Acetate) | 10 IU |
| Vitamin $K_1$ | 150 mcg |
| Dexpanthenol | 15 mg |

Example 5. Pharmaceutical Dosage Forms

The following formulations illustrate representative oral tannin dosage forms that may be used for the therapeutic or prophylactic administration of a tannin described herein (hereinafter referred to as 'PAC'):

| (i) Tablet 1 | mg/tablet |
|---|---|
| 'PAC' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'PAC' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'PAC' | 10.0 |
| Colloidal silicon dioxide | 1.5 |
| Lactose | 465.5 |
| Pregelatinized starch | 120.0 |
| Magnesium stearate | 3.0 |
| | 600.0 |

These formulations may be prepared by conventional procedures well known in the pharmaceutical art. It will be appreciated that the above pharmaceutical compositions may be varied according to well-known pharmaceutical techniques to accommodate differing amounts and types of tannin. Additionally, the specific ingredients and proportions are for illustrative purposes. Ingredients may be exchanged for suitable equivalents and proportions may be varied, according to the desired properties of the dosage form of interest.

Example 5. Cranberry Proanthocyanidins Preserves Microbiota Diversity During Elemental Enteral Nutrition The human gastrointestinal tract is colonized by over 1000 bacterial species present in enormous quantities that are collectively termed the microbiome (Guarner F. Role of intestinal flora in health and disease. *Nutr Hosp*. May 2007; 22 Suppl 2:14-19). The average microbiome may contain 10 times the number of individual cells with over 100 times the genetic diversity than its human host, highlighting the generally underappreciated role of microbes in human homeostasis and health. The microbiome plays fundamental roles in immune stimulation and maintenance, digestion, and synthesis of vitamins and short chain fatty acids that are proposed to benefit the host and is therefore implicated in influencing health (Guarner). Altered microbiome structures have been identified in states of metabolic dysfunction, such as obesity, diabetes, and inflammatory bowel diseases (Conterno L, Fava F, Viola R, Tuohy K M. Obesity and the gut microbiota: does up-regulating colonic fermentation protect against obesity and metabolic disease? *Genes Nutr*. August 2011; 6(3):241-260; and Maccaferri S, Biagi E, Brigidi P. Metagenomics: key to human gut microbiota. Dig Dis. 2011; 29(6):525-530). One key modulatory force over microbiome structure is dietary intake, such as the ratio of carbohydrates to protein intake, dietary fiber, and polyphenolics. Under parenteral or enteral feeding where enteral bulk and complexity is decreased, especially in the proximal bowel, reduced microbiome diversity is measured (Kajiura T, Takeda T, Sakata S, et al. Change of intestinal microbiota with elemental diet and its impact on therapeutic effects in a murine model of chronic colitis. *Dig Dis Sci*. September 2009; 54(9):1892-1900). The loss of microbiome diversity is associated with reduced immune parameters in the gastrointestinal tract, including decreased barrier function (Ott S J, Musfeldt M, Wenderoth D F, et al. Reduction in diversity of the colonic mucosa associated bacterial microflora in patients with active inflammatory bowel disease. Gut. May 2004; 53(5):685-693).

In investigating the role of dietary intake upon microbiome structure, recent attention has been drawn to the role of plant products, including fiber and polyphenolics (de Vrese M, Schrezenmeir J. Probiotics, prebiotics, and synbiotics. Adv Biochem Eng Biotechnol. 2008; 111:1-66). Certain fermentable fibers, such as inulin and fructooligosacharides, are known prebiotics that are proposed to modulate the intestinal microbiome composition in a way that is beneficial or protective to the host (de Vrese et al.). With the use of metabolomic analysis, microbiome metabolism of polyphenolic compounds is also beginning to be elucidated (Tuohy K M, Conterno L, Gasperotti M, Viola R. Up-regulating the Human Intestinal Microbiome Using Whole Plant Foods, Polyphenols, and/or Fiber. *J Agric Food Chem*. September 2012; 60(36):8776-8782). In contrast to some polyphenolics that are largely metabolized before exiting the colon, proanthocyanidins (PAC) remain intact during transit through the small bowel and are metabolized to lesser degrees in the large intestine (Ottaviani J I, Kwik-Uribe C, Keen C L, Schroeter H. Intake of dietary procyanidins does not contribute to the pool of circulating flavanols in humans. *Am J Clin Nutr*. April 2012; 95(4):851-858). The studies outlined in the examples above show the effect of supplementing elemental enteral nutrition (EEN) formulations with PAC to determine their effects upon gut health, including alterations to the epithelial barrier and GALT. In those studies, samples of intestinal content from the ileal-cecal junction were collected for crude analysis of the microbiome community via automated ribosomal intergenic spacer analysis (ARISA) to determine the effect of EEN and EEN supplemented with PAC upon bacterial diversity. ARISA is useful since the spacer between 16S and 23S rRNA genes of microorganisms are commonly varied in length and sequence but well conserved between species (Kovacs A, Yacoby K, Gophna U. A systematic assessment of automated ribosomal intergenic spacer analysis (ARISA) as a tool for estimating bacterial richness. *Res Microbiol*. April 2010; 161(3):192-197). ARISA has been shown to highly correlate with 16S sequencing as a tool for bacterial richness estimation (Kovacs et al.).

Materials and Methods.

PAC Preparation, Animals, and Experimental Design.

The PAC preparation and characterization, animals, and experimental design used were the same as described in Example 1 under "PAC Preparation," "PAC characterization by HPLC," "PAC characterization by matrix-assisted laser desorption/ionization time-of-flight MS (MALDI-TOF MS)," "Animals," and "Experimental Design." Additionally, during tissue harvest, luminal contents were collected with 1 mL of HBSS from the last 1 cm of small intestine and stored at −80° C. until analysis.

ARISA.

Total genomic DNA was isolated from intestinal contents using DNeasy Blood and Tissue Kit (Qiagen, Hilden, Germany) and the 16S-23S rRNA spacer was amplified as previously described by Fisher and Triplett (Fisher M M, Triplett E W. Automated approach for ribosomal intergenic spacer analysis of microbial diversity and its application to freshwater bacterial communities. *Appl Environ Microbiol*. October 1999; 65(10):4630-4636). Briefly, PCR reactions were performed in duplicate in 20 µl reactions with Taq DNA polymerase (Invitrogen, Carlsbad, Calif.), 3 uM of $MgCl_2$, 2 µl 10×PCR buffer, 0.1 mM dNTP mix, nuclease-free water, and 1 pmol of primers. The reaction sequence was as follows: 3 min at 94° C.; 30 cycles of 1 min denaturation at 94° C., 1 min annealing at 53° C., 1.25 min elongation at 72° C.; and 10 min final elongation at 72° C.

Fragment Analysis and Diversity Estimation.

A peak scanner (Applied Biosystems, Foster City, Calif.) with capillary electrophoresis was used to analyze total product peaks and data were represented as a fragment from at least one bacterial phylotype. Peaks observed between 300 and 1000 base pairs with a threshold of at least 100 fluorescent units were selected to make ARISA profiles. Data were exported to Microsoft Excel for further analysis. Since the sum of the peaks is proportional to the total DNA concentration, peaks at each fragment size were calculated as a relative amount of total DNA. Peaks that did not reach 0.5% of total DNA were removed from analysis in order to minimize false peaks that might result in overestimation of species richness. The remaining peaks were analyzed to estimate species diversity using the Shannon's diversity index and Simpsons index of diversity (1-D) in PAST (http://folk.uio.no/ohammer/past/), which both measure the richness and evenness of species present in samples. Significant differences were accepted at $P<0.05$. Next, treatment groups were compared with the Jaccard similarity coefficient, used to statistically compared similarity among groups. Finally, the peaks were analyzed using principal coordinate analysis (PCoA) (PAST), which aids to visualize changes in community structure across a primary and secondary axis and 95% confidence ellipses were determined.

Results

There were 53 total peaks (detected phylotypes) observed in Chow, while only 22 peaks were observed in EEN (Table 5-1). There were 40 total peaks observed in EEN+PAC. After removing peaks that did not reach greater than 0.5% of total signal, there were 32 peaks in Chow (FIG. 11A), 15 in EEN (FIG. 11B), and 25 in EEN+PAC (FIG. 11C). Overall, the peaks appeared more similar between Chow and EEN+PAC and either group compared to EEN alone. This was tested across the entire data set statically using peaks greater than 0.5% of total signal and calculating Jaccard's similarity coefficient. This similarity analysis revealed that the peak profiles of Chow and EEN+PAC are 65% similar to one another, while both dietary groups are only about 50% similar to EEN alone (FIG. 12). To compare diversity, we calculated the Shannon's diversity index (SH) and Simpsons index of diversity (SI) between each group. Compared with Chow (SH 3.8; SI 0.891), EEN significantly reduced diversity (SH 2.56, $P<0.01$; SI 0.85, $P<0.05$). Compared with EEN, the addition of PAC to EEN significantly increased diversity (SH 3.46, $P<0.01$; SI 0.91, $P<0.05$). When comparing Chow to EEN+PAC, diversity differences were detected with SH ($P<0.05$) but not SI ($P=0.19$). Finally, principal coordinate analysis revealed slight shifts in composition using Unifrac distance metrics, but striking differences were observed since 95% confidence intervals overlapped (FIG. 13).

TABLE 5-1

Comparison of total, >1%, and >0.5% peaks observed (estimated phylotypes) in ileum content samples measured via ARISA.

| Group | Numbers of phylotypes present | Numbers of phylotypes present greater than 1% | Numbers of phylotypes present greater than 0.5% | Numbers of novel phylotypes relative to Chow |
|---|---|---|---|---|
| Chow | 53 | 33 | 32 | — |
| EEN | 22 | 16 | 15 | 2 |
| EEN + PAC | 40 | 30 | 25 | 8 |

Discussion

The relationship between diet, microbiome composition, and health is receiving more attention as a testable hypothesis following the development of methods able to measure the interplay between bacterial composition and host metabolism (Tuohy et al.; Moco et al.). Polyphenolics are a prime target for these investigations since epidemiologic studies have repeatedly identified greater polyphenolic intake with lower incidence of chronic diseases (Scalbert A, Manach C, Morand C, Remesy C, Jimenez L. Dietary polyphenols and the prevention of diseases. *Crit Rev Food Sci Nutr.* 2005; 45(4):287-306). In this study, we employed a crude method of microbial analysis, ARISA, to determine the effects of EEN or EEN supplemented with PAC upon microbiome diversity. We used ARISA since this method is cost effective and correlates well with more detailed sequencing methods to determine species diversity across samples (Kovacs et al.). Consistent with previous work using EEN, we observed a decrease in microbiome diversity compared with Chow feeding (Kajiura et al.). Interestingly, the addition of PAC to EEN resulted in a partial maintenance of diversity compared with EEN alone. These findings suggest PAC may support microbiome structure as dietary compounds. These data build upon Examples 1 and 2, demonstrating beneficial effects of PAC supplementation to EEN upon the intestinal epithelium and GALT function.

Example 6. A-Type Proanthocyanidins (A-PAC), B-Type Proanthocyanidins (B-PAC), and Oligomeric Hydrolysable Tannins (OHT) Attenuate the Effects of Elemental Enteral Nutrition on Size, Density, and Function of Intestinal Goblet Cells in Mice As outlined in Examples 1 and 2 above, addition of proanthocyanidin tannins to a clinically used elemental enteral nutrition (EEN) solution counteracts the impairment of the intestinal immune barrier function. In those examples, a class of tannins, called A-type proanthocyanidins (A-PAC) (from cranberry fruit), were used. The present example shows that other major types of tannins, B-type proanthocyanidins (B-PAC) and oligomeric hydrolyzable tannins (OHT), produce comparable effects when added to an EEN solution.

Materials and Methods

Experimental Methodology.

Cranberry fruit, grape seeds and pomegranate were used as sources for isolation of A-PAC, B-PAC and OHT, respectively. Isolation (liquid chromatography) and characterization (MALDI-TOF mass spectrometry) techniques were used to first separate the three distinct tannin preparations. The isolation was performed as described in Example 1 under "PAC Preparation," except that grape seeds and pomegranate husk were used for preparation of B-PAC and OHT, respectively. Cranberry presscake was used for preparation of A-PAC. The characterization was performed as described in Example 1 under "PAC characterization by matrix-assisted laser desorption/ionization time-of-flight MS (MALDI-TOF MS)." The effects of the three EEN formulations on the intestinal immune barrier function were tested in a mouse model, as described in Example 1 under "Animals" and "Experimental Design," except that the A-PAC, B-PAC or OHT was administered at a dose of 100 mg tannins/kg bodyweight/day. Analysis of ileal cytokines was performed as described in Example 1 under "Analysis of ileal IL-4 and IL-13." Analysis of luminal MUC2 was performed as described in Example 1 under "Analysis of luminal MUC2." Histomorphometic analysis was performed as described in Example 1 under "Analysis of GC density and size." Statistical analysis was performed as described in Example 1 under "Statistical analysis." Microbiota diversity was performed using methods as described in Example 5.

Results.

Preliminary data indicates that, similar to the A-PAC cranberry tannins shown in Example 1, the addition of B-PAC and OHT to enteral formulation significantly protects against the morphological atrophy of the gastrointestinal tissue induced by the consumption of the enteral formulation alone.

Discussion.

It is predicted that B-PAC tannins and OHT have each of the same effects shown for A-PAC. Specifically, it is predicted that B-PAC tannins and OHT protect against EEN- and PN-dependent reductions in IL-4 and IL-13, goblet cell density and size, luminal MUC2 levels, Peyer's patch lymphocytes, phosphorylated STAT6, pIgR, sIgA, and microbiota diversity. It is surmised that a shared structural feature among the tannins (oligomeric phenolic structure), and not a distinct structural feature of the respective tannins (A-type interflavan bonds, B-type interflavan bonds, or ester bonds), is responsible for improving intestinal immune barrier function. That is, the source of tannin is irrelevant.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method to attenuate deleterious effects of enteral nutrition on intestinal barrier function comprising administering an effective amount of one or more proanthocyanidins to a subject receiving enteral nutrition, wherein the one or more proanthocyanidins have a degree of polymerization of at least 2.

2. The method of claim 1, wherein the administering comprises administering a composition comprising the effective amount of the one or more proanthocyanidins and comprising no monomeric tannin components or less than about 5 wt. % monomeric tannin components.

3. The method of claim 1, wherein the administering comprises administering the one or more proanthocyanidins in an amount of from about 1 µg/kg of subject body weight to about 100 mg/kg of subject body weight, per day.

4. The method of claim 1, wherein the administering comprises administering the one or more proanthocyanidins in an amount of from about 5 mg/kg of subject body weight to about 10 mg/kg of subject body weight, per day.

5. The method of claim 1, wherein the effective amount is an amount effective to result in one or more of increased levels of ileal IL-4, increased levels of ileal IL-13, increased density of goblet cells, increased goblet cell size, increased relative luminal MUC2 concentration, inhibited reduction of phosphorylated STAT6, inhibited reduction of polymeric immunoglobulin receptor (pIgR), and increased luminal secretory immunoglobulin-A (sIgA) levels compared to administering enteral nutrition nutrition without the effective amount of the one or more proanthocyanidins.

6. The method of claim 1, wherein the subject is a subject receiving elemental enteral nutrition.

7. The method of claim 1, wherein the subject is a subject receiving elemental enteral nutrition via tube feeding.

8. The method of claim 1, wherein the subject is a subject receiving nutrition only from elemental enteral nutrition.

9. The method of claim 1, wherein the subject is a subject comprising a condition selected from the group consisting of inflammatory bowel disease, sepsis, and trauma.

10. The method of claim 1, wherein the subject is a subject suffering from burn.

11. The method of claim 1, wherein the subject is a pre-surgery patient or a post-surgery patient.

12. The method of claim 1, wherein the subject is a subject with acute or chronic illness.

13. The method of claim 1, wherein the subject is a subject receiving nutrition only in a liquid form.

14. The method of claim 1, wherein the subject is a subject with a contraindication to normal feeding and is administered the enteral nutrition as a liquid diet.

15. The method of claim 1, wherein the administering comprises administering a liquid composition comprising the effective amount of the one or more proanthocyanidins and a protein source constituting at least 20% of total calories of the composition.

16. The method of claim 1, wherein the administering comprises administering a liquid composition comprising the effective amount of the one or more proanthocyanidins and a component selected from the group consisting of protein and amino acids, wherein the component constitutes about 17-25% of total calories of the composition.

17. The method of claim 1, wherein the administering comprises administering a liquid composition having a caloric density of at least 1 Kcal/mL.

* * * * *